(12) United States Patent
Gjerde et al.

(10) Patent No.: US 6,521,123 B2
(45) Date of Patent: *Feb. 18, 2003

(54) POLYNUCLEOTIDE SEPARATIONS ON POLYMERIC SEPARATION MEDIA

(75) Inventors: Douglas T. Gjerde, Saratoga, CA (US); Paul D. Taylor, Palo Alto, CA (US); Robert M. Haefele, Palo Alto, CA (US)

(73) Assignee: Transgenomic, Inc., San Jose, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 09/848,385

(22) Filed: May 2, 2001

(65) Prior Publication Data

US 2001/0032817 A1 Oct. 25, 2001

Related U.S. Application Data

(60) Division of application No. 09/493,779, filed on Jan. 28, 2000, now Pat. No. 6,309,549, which is a continuation of application No. 09/183,123, filed on Oct. 30, 1998, now Pat. No. 6,066,258, which is a continuation-in-part of application No. 09/058,580, filed on Apr. 10, 1998, now abandoned, which is a continuation-in-part of application No. 08/748,376, filed on Nov. 13, 1996, now Pat. No. 5,772,889.

(51) Int. Cl.[7] .............................................. B01D 15/08
(52) U.S. Cl. ............................ 210/198.2; 210/502.1; 210/635; 210/656; 435/6; 536/25.4
(58) Field of Search .................................. 210/635, 656, 210/659, 198.2, 502.1; 435/6; 536/23.1, 25.4; 502/401, 402, 404

(56) References Cited

U.S. PATENT DOCUMENTS 5,583,162 A    12/1996  Li ................................ 521/56
5,645,717 A    7/1997   Hjerten ...................... 210/198.2
5,647,979 A    7/1997   Liao .......................... 210/198.2
5,728,457 A    3/1998   Frechet et al. ........... 428/310.5

(List continued on next page.)

FOREIGN PATENT DOCUMENTS

| EP | 0 813 062 A2   | 4/1997  | ................. 210/635 |
|----|----------------|---------|--------------------------|
| WO | WO 90/07965 A1 | 7/1990  | ................. 210/635 |
| WO | WO 95/343359   | 12/1995 | ................. 210/635 |
| WO | WO 97/19347    | 5/1997  | ................. 210/635 |
| WO | WO 00/15778    | 3/2000  | ................. 210/635 |
| WO | WO 01/55713 A2 | 8/2001  | ................. 210/635 |
| WO | WO 01/83072 A1 | 11/2001 | ................. 210/635 |

OTHER PUBLICATIONS

Apffel, et al., Analysis of Oligonucleotides by HPLC–Electrospray Ionization Mass Spectrometry, Anal. Chem. 1997, 69, 1320–1325.

Ericson, et al., Preparation of Continuous Beds for Electrochromatography and Reversed–Phase Liquid Chromatography of Low–Molecular–Mass, Journal of Chromatography A, 767:33–41 (1997).

Fields, Silica Xerogel as a Continuous Column Support for High–Performance Liquid Chromatography, Anal. Chem. 68:2709–2712 (1996).

(List continued on next page.)

Primary Examiner—Ernest G. Therkorn

(57) ABSTRACT

Non-polar polymeric separation media, such as beads or monoliths, are suitable for chromatographic separation of mixtures of polynucleotides when the surfaces of the media are unsubstituted or substituted with a hydrocarbon group having from one to 1,000,000 carbons and when the surfaces are substantially free from mutivalent cation contamination. The polymeric media provide efficient separation of polynucleotides using Matched Ion Polynucleolide Chromatography. Methods for maintaining and storing the polymeric media include treatment with multivalent cation binding agents.

24 Claims, 11 Drawing Sheets

U.S. PATENT DOCUMENTS

| | | | | |
|---|---|---|---|---|
| 5,929,214 | A | 7/1999 | Peters | 530/417 |
| 5,972,222 | A | 10/1999 | Gjerde et al. | 210/635 |
| 5,998,604 | A | 12/1999 | Fearon et al. | 536/25.4 |
| 6,024,878 | A | 2/2000 | Gjerde et al. | 210/635 |
| 6,056,877 | A | 5/2000 | Gjerde et al. | 210/635 |
| 6,066,258 | A | 5/2000 | Gjerde et al. | 210/635 |
| 6,174,441 | B1 | 1/2001 | Gjerde et al. | 210/635 |
| 6,238,565 | B1 | 5/2001 | Hatch | 210/635 |
| 6,309,549 | B1 | 10/2001 | Gjerde et al. | 210/635 |
| 6,355,791 | B1 * | 3/2002 | Gjerde | 536/25.4 |
| 6,372,130 | B1 * | 4/2002 | Gjerde | 210/198.2 |
| 6,372,142 | B1 | 4/2002 | Gjerde et al. | 210/635 |

OTHER PUBLICATIONS

Fujimoto, et al., Fritless Packed Columns for Capillary Electrochromatography: Separation of Uncharged Compounds on Hydrophobic Hydrogels, Anal. Chem. 68:2753–2757 (1996).

Fujimoto, et al., Capillary Electrochromatography of Small Molecules in Polyacryamide Gels with Electroosmotic Flow, Journal of Chromatography A, 716 107–113 (1995).

Giovannini, et al., Anal. Chem. 70:3348–3354 (1998).

Griffey, et al., Characterization of Oligonucleotide Metabolism in Vivo Via Liquid Chromatography/Electrosspray Tandem Mass Spectrometry with a Quadrupole Ion Trap Mass Spectrometry, Journal of Mass Spectrometry, 32: 305–313 (1997).

Gusev, et al., Capillary Columns with in Situ Formed Porous Monolithic Packing for Micro High–Performance Liquid Chromatography and Capillary Electrochromatography, Journal of Chromatography A, 855: 273–290 (1999).

Hansen, et al., Highly Permeable Open–Pore Polyurethane Columns for Liquid Chromatography, Journal of Chromatography, 99:123–133 (1974).

Hjerten, et al., High–Performance Liquid Chromatography on Continuous Polymer Beds, Journal of Chromatography, 473:273–275 (1989).

Hjerten, et al., Continuous Beds: High–Resolving, Cost–Effective Chromatographic Matrices, Nautre 356: 810–811 (1992).

http://www.thermoquest.com/SJ_Y2K.HTML Dec. 12, 2000.

Huber, et al., A Comparison of Micropellicular Anion–Exchange and Reversed–Phase Stationary Phases for HPLC Analysis of Oligonucleotides, LC–GC 14:114–127 (1996).

Huber, et al., Sheath Liquid Effects Capillary High–Performance Liquid Chromatography–Electrospray Mass Spectrometry of Oligonucleotides, Journal of Chromatography A, 870:413–424 (2000).

Huber, et al., Mutation Detection by Capillary Denaturing High–Performance Liquid Chromatography Using Monolithic Columns, J. Biochem. Biophys Methods 47:5–19 (2001).

Huber, et al., On–Line Cation Exchange for Suppression of Adduct Formation in Negative–Ion Electrospray Mass Spectrometry of Nucleic Acids, Anal. Chem. 70:5288–5295 (1998).

Huber, et al., Evaluation of Volatile Eluents and Electrolytes for High–Performance Liquid Chromatography–Electrospray Ionization Mass Spectrometry and Capillary Electrophoresis–Electrospray Ionization Mass Spectrometry of Proteins, I. Liquid Chromatography, Journal of Chromatography A, 849: 161–173 (1999).

Huber et al, Analysis of Nucleic Acids by Capillary Ion–Pair Reversed–Phase HPLC Coupled to Negative–Ion Electrospray Ionization Mass Spectrometry, Anal. Chem. 71: 3730–3739, (1999).

Ishizuka, et al., Chromatography Properties of Miniaturized Silica Rod Columns, J. High Resol. Chromatogr. 21:477–479 (1998).

Leonard, M., New Packing Materials For Protein Chromatography, Journal of Chromatography B, 699:3–27 (1997).

Liao, et al., Anal. Biochem. 234:27–30 (1996).

McLuckey, et al., Tandem Mass Spectrometry of Small, Multiply Charged Oligonucleotides, j. Am. Soc. Mass Spectrom. 3:60–70 (1992).

Minakuchi, et al., Octadecylsilylated Porous Silica Rods as Separation Media for Reversed–Phase Liquid Chromatography, Anal. Chem. 68:3498–3501 (1996).

Moore, R., et al., A Microscale Electrospray Interface Incorporating A Monolithic, Poly (styrene–divinylbenzene) Support for On–Line Liquid Chromatography/Tandem Mass Spectrometry Analysis of Peptides and Proteins, Anal. Chem. 70:4879–4884 (1998).

Muddiman, et al., Precise Mass Measurement of a Double–Stranded 500 Base–Pair (309 kDa) Polymerase Chain Reaction Product by Negative Ion Electrospray Ionization Fourier Transform Ion Cyclotron Resonance Mass Spectrometry, Rapid Commun. Mass Spectrom. 13, 1201–1204 (1999).

Nordhoff, et al., Mass Spectrometry of Nucleic Acids, Mass Spectrometry Reviews, 15:67–138 (1996).

Oberacher, et al., Preparation and Evaluation of Packed Capillary Columns for the Separation of Nucleic Acids by Ion–Pari Reversed–Phase High–Performance Liquid Chromatography, J. of Chrom. A 893:23–25 (2000).

Palm, et al., Macroporous Polyacrylamide/Poly (Ethylene Glycol) Matrixes as Stationary Phases in Capillary Electrochromatography, Anal. Chem. 69:4499–4507 (1997).

Peters, et al., Molded Rigid Polymer Monoliths as Separation Media for Capillary Electrochromatography, Anal. Chem. 69:3645–3649 (1997).

Peters, et al., Molded Rigid Polymer Monoliths as Separation Media for Capillary Electrochromatography. 2. Effect of Chromatographic Conditions on the Separation, Anal. Chem. 70:2296–2302 (1998).

Petro, et al., Molded Continuous Poly (styrene–co–divinylbenzene) Rod as a Separation Medium for the Very Fast Separation of Polymers Comparison of the Chromatographic Properties of the Monolithic Rod With Columns Packed With Porous and Non–Porous Beads in High–Performance Liquid Chromatography of Polystyrenes, Journal of Chromatography A, 752:59–66 (1996).

Ponten, et al., Anal. Chem. 68:4369–4396 (1996).

Potier, et al., Negative Electrospray Ionization Mass Spectrometry of Synthetic and Chemically Modified Oligonucleotides, Nucleic Acids Research, 22:3895–3903 (1994).

Premstaller, et al. High–Performance Liquid Chromatography–Electrospray Ionization Mass Spectrometry of Single––And Double–Stranded Nucleic Acids Using Monolithic Capillary Columns Anal. Chem. 72:4386–4393 (2000).

Rabel, et al., Advancing Separation Science with Monolithic Silica HPLC Columns, American Laboratory, 20–22 (Dec. 2000).

Seidl, et al., Markoporose Styrol–Divinylbenzol–Copolymere Und Ihre Verwendung in der Chromatographie und zue Darstellung von Ionenaustauschern, Adv. Polymer Sci. 5:113–213 (1967).

Stults, et al., Improved Electrospray Ionization of Synthetic Oligodeoxynucleotides, Rapid Communication in Mass Spectrometry, vol. 5:359–363 (1991).

Suck, et al., The Structure of a Trinucleoside Diphosphate:Adenylyl–(3',5")–Adenylyl–(3',5')–Adenosine Hexahydrate, Acta Cryst. B 32:1727–1737 (1976).

Svec, et al., Temperature, A Simple and Efficient Tool for the Control of Pore Size Distribution in Macroporous Polymers, Macromolecules 25:7580–7582 (1995).

Tennikova, et al., An Introduction to Monolithic Disks as Stationary Phases for High Performance Biochromatography, J. High Resol. Chromatogr. 23:(1)27–38 (2000).

Thermoquest LC/MS Application Report (1999).

Tomer, et al., Capillary Liquid Chromatography/Mass Spectrometry, Mass Spectrometry Reviews, 13:431–457 (1994).

Viklund, et al., Monolithic, "Molded", Porous Materials with High Flow Characteristics for Separations, Catalysis, or Solid–Phase Chemistry: Control of Porous Properties During Polymerization, Chem. Mater. 8:744–750 (1996).

Viklund, et al., Chem. Mater. 9:463–471 (1997).

Xiao et al, Multiplex Capillary Denaturing High–Performance Liquid Chromatography with Laser–Induced Flurorescense Detection, Bio Techniques 30:1332–1338 (Jun. 2001).

U.S. patent application Ser. No. 09/770,410, Huber, et al., filed Jul. 11, 2002.

U.S. patent application Ser. No. 09/828,427, Gjerde, et al., filed Oct. 18, 2002.

U.S. patent application Ser. No. 10/085,691, Gjerde, et al., filed Nov. 28, 2002.

U.S. patent application Ser. No. 10/092,410, Gjerde, et al., filed Mar. 4, 2002.

Huber, Micropellicular Stationary Phases For High–Performance Liquid Chromatography Of Double–Stranded DNA, J. of Chromatography A, 806:1–30 (1998).

* cited by examiner

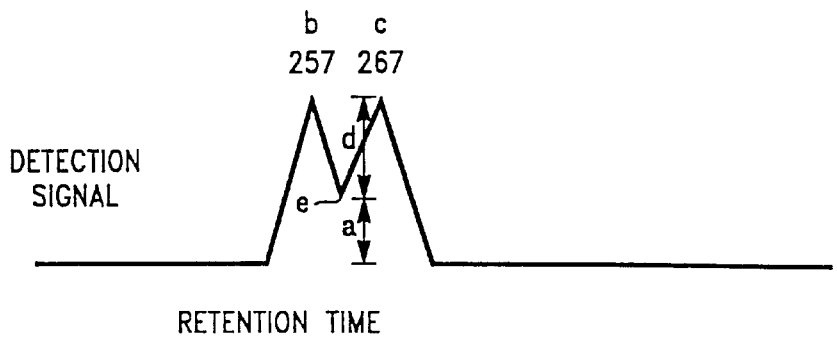
FIG.—1
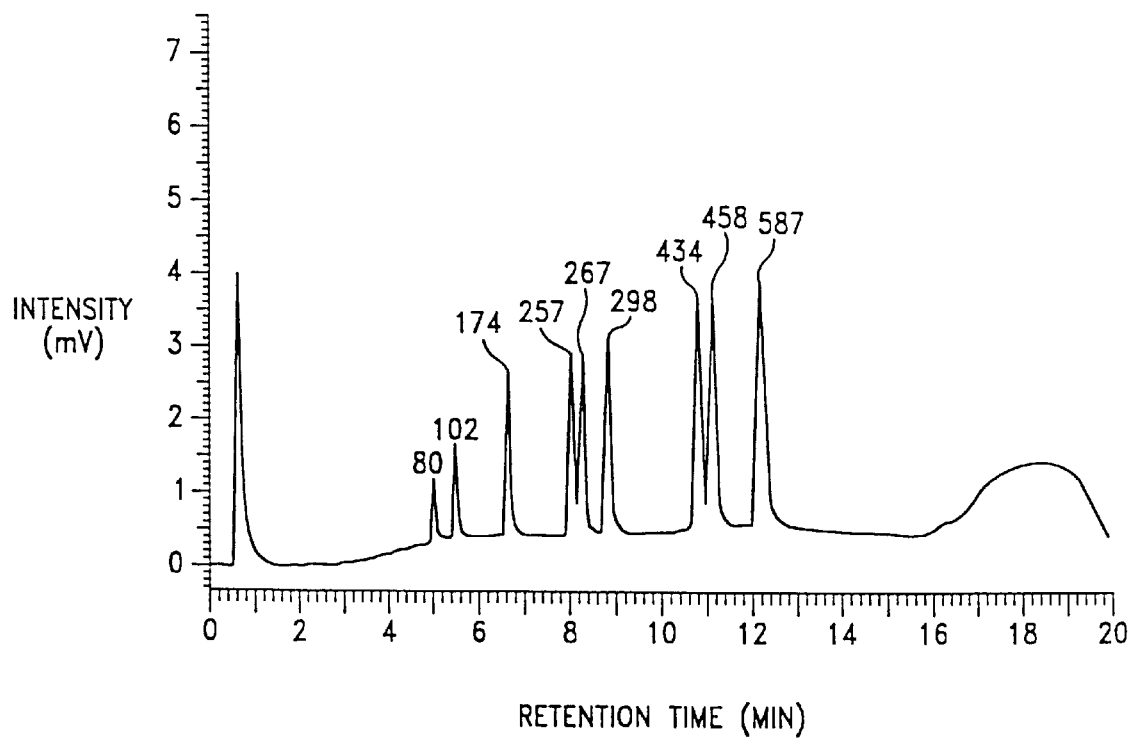
FIG.—2

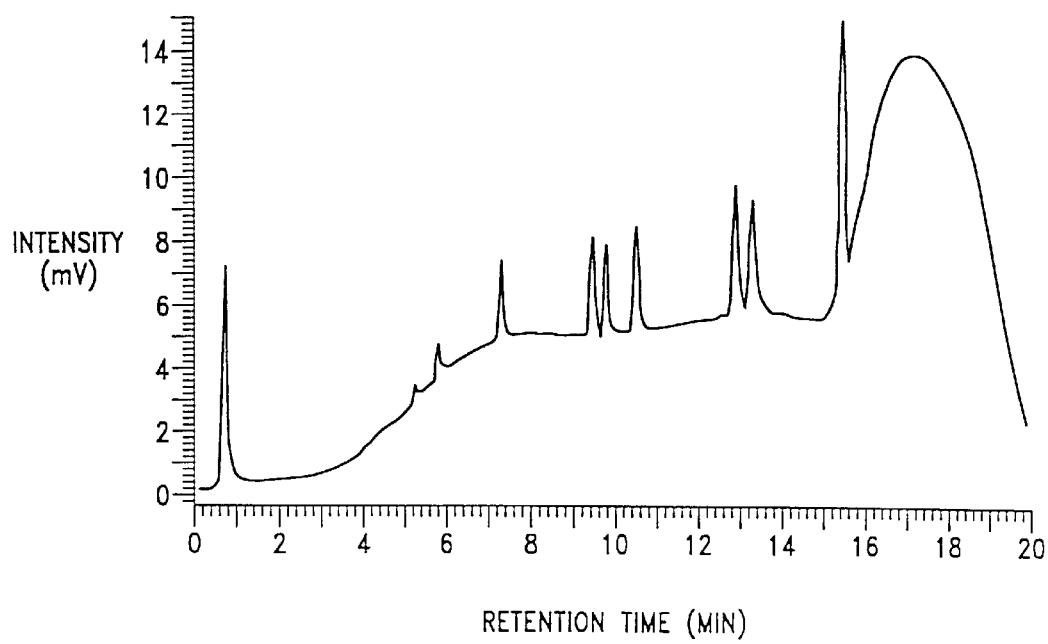
FIG.—3
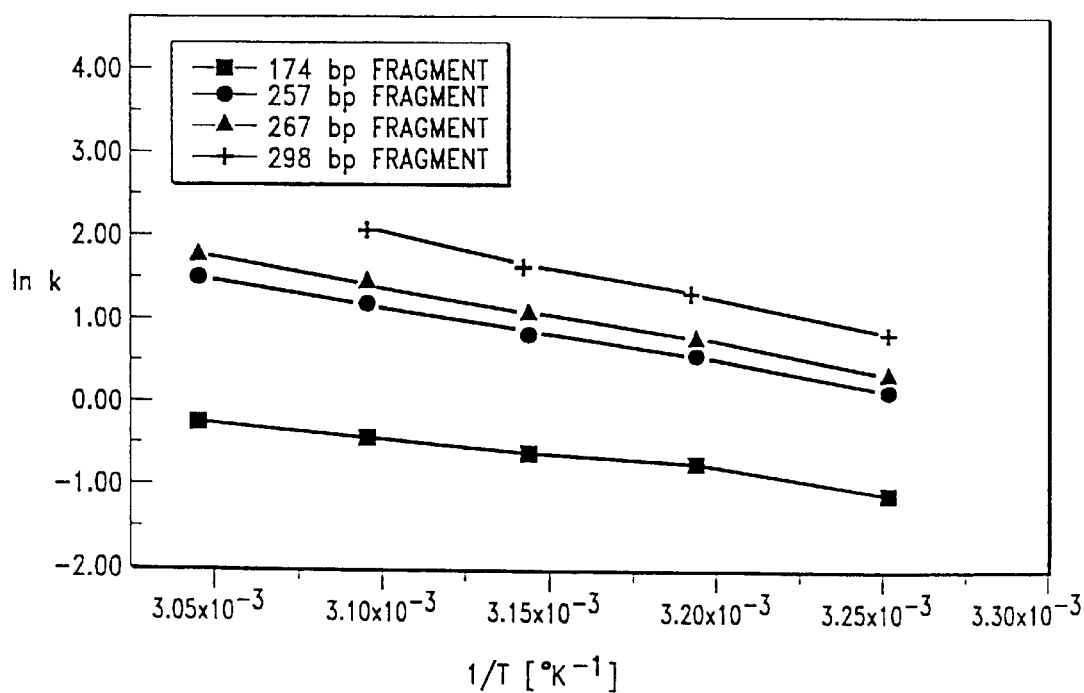
FIG.—4

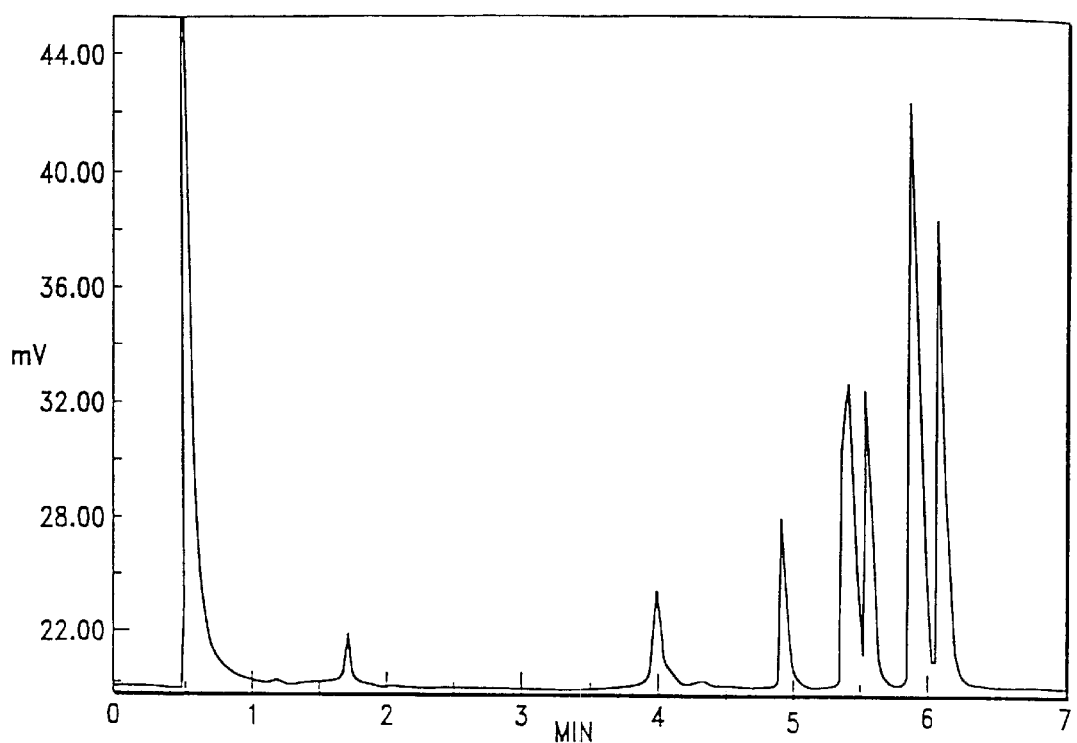
FIG.—15
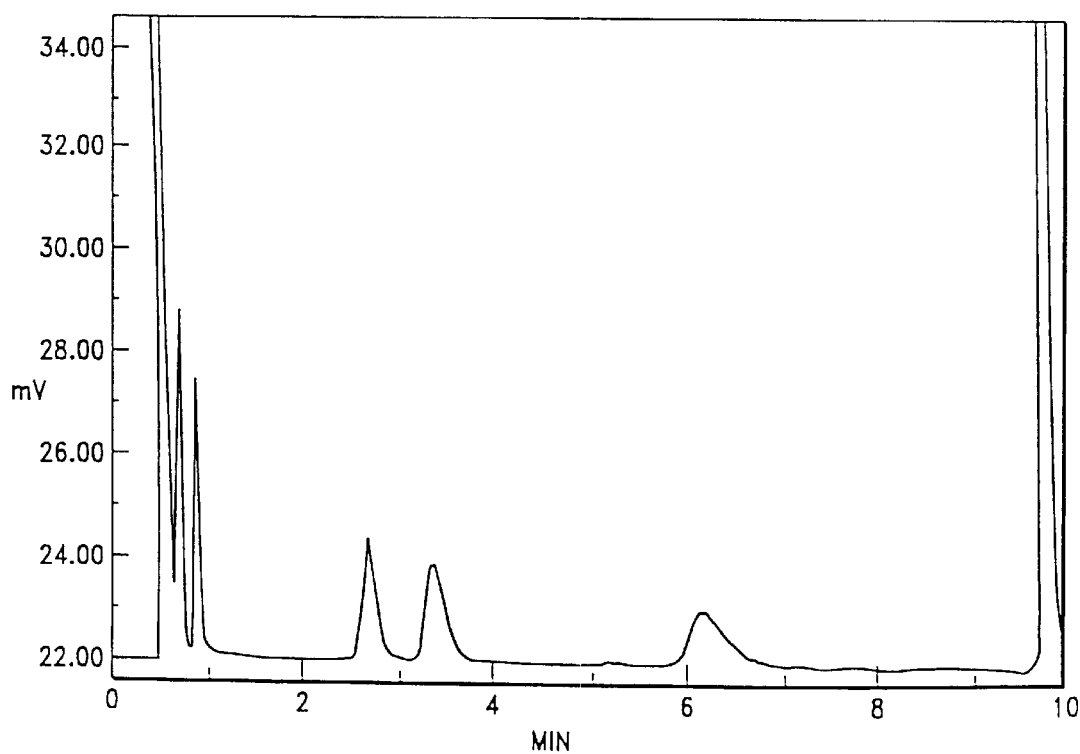
FIG.—16

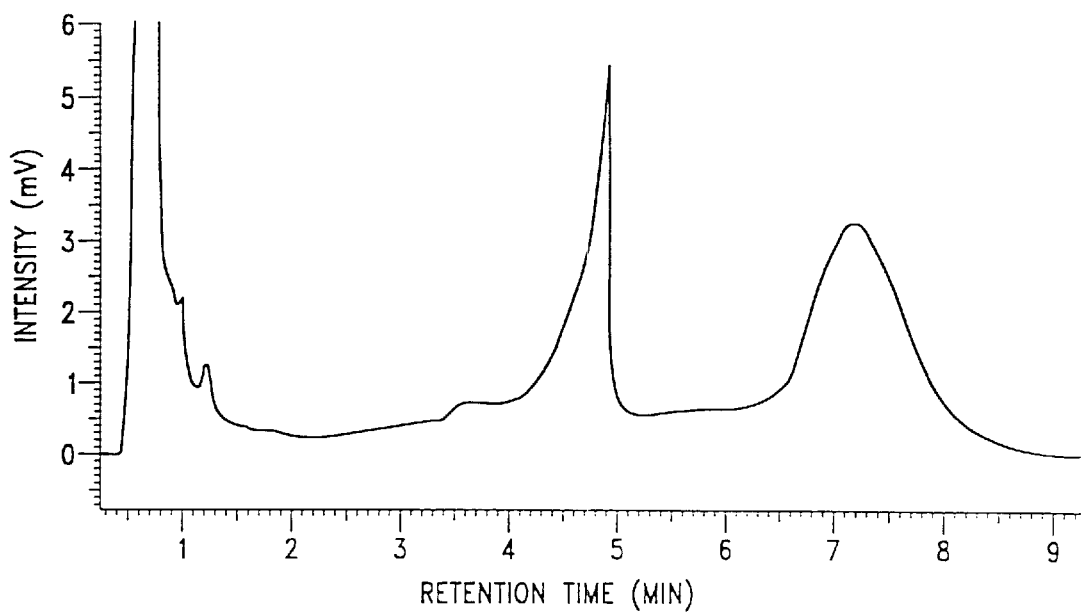
FIG.—21
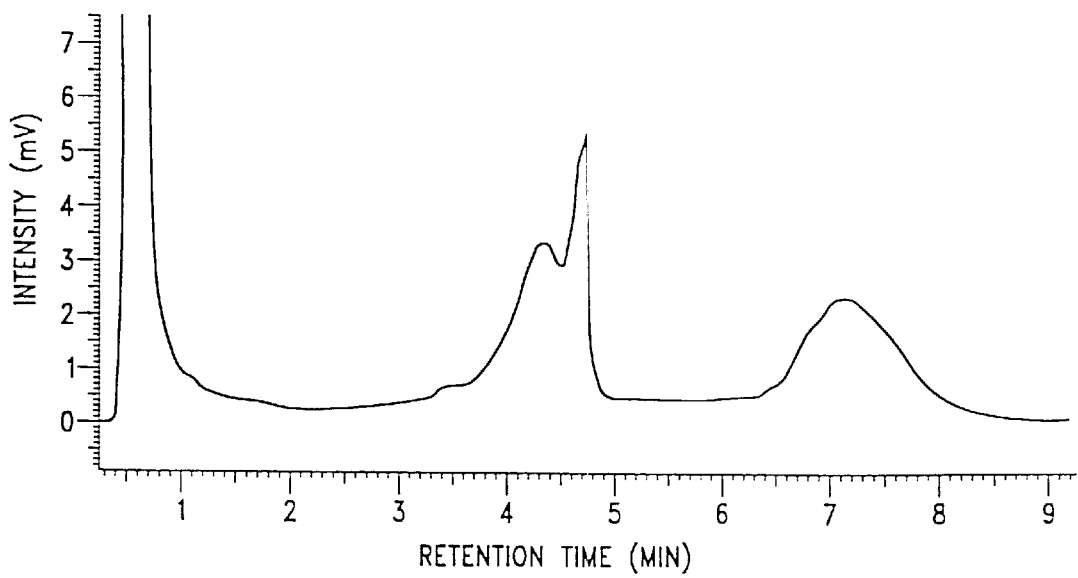
FIG.—22

POLYNUCLEOTIDE SEPARATIONS ON POLYMERIC SEPARATION MEDIA

CROSS-REFERENCE TO RELATED APPLICATIONS

This is a divisional application of U.S. patent application Ser. No. 09/493,779 filed Jan. 28, 2000 (now U.S. Pat. No. 6,309,549), which a continuation application of U.S. patent application Ser. No. 09/183,123 filed Oct. 30, 1998 (now U.S. Pat. No. 6,066,258), which is a continuation-in-part application of U.S. patent application Ser. No. 09/058,580 filed Apr. 10, 1998 (abandoned), which is a continuation-in-part application of U.S. patent application Ser. No. 08/748,376 filed Nov. 13, 1996 (now U.S. Pat. No. 5,772,889), which are hereby incorporated by reference in their entirety. This application is a regular U.S. patent application under 35 U.S.C. §111(a) and 37C.F.R. §1.53(b).

FIELD OF THE INVENTION

The present invention is directed to the separation of polynucleotides using non-polar separation surfaces, such as the surfaces of polymeric beads and surfaces within molded monoliths, which are substantially free from contamination with multivalent cations.

BACKGROUND OF THE INVENTION

Separations of polynucleotides such as DNA have been traditionally performed using slab gel electrophoresis or capillary electrophoresis. However, liquid chromatographic separations of polynucleotides are becoming more important because of the ability to automate the analysis and to collect fractions after they have been separated. Therefore, columns for polynucleotide separation by liquid chromatography (LC) are becoming more important.

High quality materials for double stranded DNA separations previously have been based on polymeric substrates disclosed in U.S. Pat. No. 5,585,236, to Bonn, et al. (1996), which showed that double-stranded DNA can be separated on the basis of size with selectivity and performance similar to gel electrophoresis using a process characterized as reverse phase ion pairing chromatography (RPIPC). However, the chromatographic material described was limited to nonporous beads substituted with alkyl groups having at least 3 carbons because Bonn, et al. were unsuccessful in obtaining separations using polymer beads lacking this substitution. Additionally, the polymer beads were limited to a small group of vinyl aromatic monomers, and Bonn et al. were unable to effect double stranded DNA separations with other materials.

A need continues to exist for chromatographic methods for separating polynucleotides with improved separation efficiency and resolution.

SUMMARY OF THE INVENTION

Accordingly, one object of the present invention is to provide a chromatographic method for separating polynucleotides with improved separation and efficiency.

Another object of the present invention is to provide a method for separating polynucleotides using nonporous polymer separation media, such as beads or monoliths (e.g., rods), having non-reactive, non-polar surfaces.

It is another object of this invention to provide the chromatographic separation of polynucleotides using non-porous polymeric separation media made from a variety of different polymerizable monomers.

It is a further object of this invention to provide the chromatographic separation of polynucleotides using polymeric separation media which can be unsubstituted, methyl-substituted, ethyl-substituted, hydrocarbon-substituted, or hydrocarbon polymer-substituted.

Yet another object of the present invention is to provide improved polymer separation media by including steps to remove contamination occurring during the manufacturing process.

Still another object of the invention is to provide a method for separating polynucleotides using a variety of different solvent systems.

These and other objects which will become apparent from the following specification have been achieved by the present invention.

In one aspect, the invention is a method for separating a mixture of polynucleotides by applying a mixture of polynucleotides having up to 1500 base pairs to a polymeric separation medium having non-polar surfaces which are substantially free from contamination with multivalent cations, and eluting the mixture of polynucleotides. The preferred surfaces are nonporous. The non-polar surfaces can be enclosed in a column. In the preferred embodiment, precautions are taken during the production of the medium so that it is substantially free of multivalent cation contaminants and the medium is treated, for example by an acid wash treatment and/or treatment with multivalent cation binding agent, to remove any residual surface metal contaminants. The preferred separation medium is characterized by having a DNA Separation Factor (defined hereinbelow) of at least 0.05. The preferred separation medium is also characterized by having a Mutation Separation Factor (as defined hereinbelow) of at least 0.1. In the preferred embodiment, the separation is made by Matched Ion Polynucleotide Chromatography (MIPC, as defined hereinbelow). Examples of non-polar surfaces include the surfaces of polymer beads and the surfaces of interstitial spaces within a polymeric monolith. The elution step preferably uses a mobile phase containing a counterion agent and a water-soluble organic solvent. Examples of a suitable organic solvent include alcohol, nitrile, dimethylformamide, tetrahydrofuran, ester, ether, and mixtures of one or more thereof, e.g., methanol, ethanol, 2-propanol, 1-propanol, tetrahydrofuran, ethyl acetate, acetonitrile. The most preferred organic solvent is acetonitrile. The counterion agent is preferably selected from the group consisting of lower alkyl primary amine, lower alkyl secondary amine, lower alkyl tertiary amine, lower trialkyammonium salt, quaternary ammonium salt, and mixtures of one or more thereof. Non-limiting examples of counterion agents include octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetrapropylammonium acetate, tetrabutylammonium acetate, dimethydiethylammonium acetate, triethylammonium acetate, tripropylammonium acetate, tributylammonium acetate, tetraethylammonium acetate, tetrapropylammonium acetate, tetrabutylammonium acetate, and mixtures of any one or more of the above. The counterion agent includes an anion, e.g., acetate, carbonate, bicarbonate, phosphate, sulfate, nitrate, propionate, formate, chloride, perchlorate, or bromide. The most preferred counterion agent is triethylammonium acetate or triethylammonium hexafluoroisopropyl alcohol.

One embodiment of the invention provides a method for separating a mixture of polynucleotides, comprising applying a mixture of polynucleotides having up to 1500 base pairs to polymeric separation beads having non-polar surfaces which are substantially free from contamination with multivalent cations, and eluting said mixture of polynucleotides. In a particular embodiment of the separation medium, the invention provides a method for separating a mixture of polynucleotides comprising flowing a mixture of polynucleotides having up to 1500 base pairs through a separation column containing polymer beads which are substantially free from contamination with multivalent cations and having an average diameter of 0.5 to 100 microns, and separating the mixture of polynucleotides. The beads are preferably made from polymers, including mono- and di-vinyl substituted aromatic compounds such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly(styrene-divinylbenzene) and poly(ethylvinylbenzene-divinylbenzene). The polymer can be unsubstituted, or substituted with a hydrocarbon such as an alkyl group having from 1 to 1,000,000 carbons. In a preferred embodiment, the hydrocarbon is an alkyl group having from 1 to 24 carbons. In more preferred embodiment, the alkyl group has 1–8 carbons. The beads preferably have an average diameter of about 1–5 microns. In the preferred embodiment, precautions are taken during the production of the beads so that they are substantially free of multivalent cation contaminants and the beads are treated, for example by an acid wash treatment, to remove any residual surface metal contaminants. The beads of the invention are characterized by having a DNA Separation Factor of at least 0.05. In a preferred embodiment, the beads are characterized by having a DNA Separation Factor of at least 0.5. Also in a preferred embodiment, the beads are characterized by having a Mutation Separation Factor of at least 0.1. The preferred method used in the separation is made by MIPC. In one embodiment, the beads are used in a capillary column to separate a mixture of polynucleotides by capillary electrochromatography. In other embodiments, the beads are used to separate the mixture by thin-layer chromatography or by high-speed thin-layer chromatography.

In addition to the beads (or other media) themselves being substantially metal-free, Applicants have also found that to achieve optimum peak separation the inner surfaces of the separation column (or other container) and all process solutions held within the column or flowing through the column are preferably substantially free of multivalent cation contaminants. This can be achieved by supplying and feeding solutions entering the separation column with components which have process solution-contacting surfaces made of material which does not release multivalent cations into the process solutions held within or flowing through the column, in order to protect the column from multivalent cation contamination. The process solution-contacting surfaces of the system components are preferably material selected from the group consisting of titanium, coated stainless steel, and organic polymer.

For additional protection, multivalent cations in mobile phase solutions and sample solutions entering the column can be removed by contacting these solutions with multivalent cation capture resin before the solutions enter the column to protect the separation medium from multivalent cation contamination. The multivalent capture resin is preferably cation exchange resin and/or chelating resin. The method of the present invention can be used to separate double stranded polynucleotides having up to about 1500 to 2000 base pairs. In many cases, the method is used to separate polynucleotides having up to 600 bases or base pairs, or which have up to 5 to 80 bases or base pairs. The mixture of polynucleotides can be a polymerase chain reaction product. The method preferably is performed at a temperature within the range of 20° C. to 90° C. The flow rate of mobile phase preferably is adjusted to yield a back-pressure not greater than 5000 psi. The method preferably employs an organic solvent that is water soluble. The method also preferably employs a counterion agent.

In another aspect, the present invention provides a polymeric bead having an average bead diameter of 0.5–100 micron. Precautions are taken during the production of the beads so that they are substantially free of multivalent cation contaminants and the beads are treated, for example by an acid wash treatment, to remove any residual surface metal contaminants. In one embodiment, the beads are characterized by having a DNA Separation Factor of at least 0.05. In a preferred embodiment, the beads are characterized by having a DNA Separation Factor of at least 0.5. In a preferred embodiment, the beads are characterized by having a Mutation Separation Factor of at least 0.1. The bead preferably has an average diameter of about 1–10 microns, and most preferably has an average diameter of about 1–5 microns. The bead can be comprised of a copolymer of vinyl aromatic monomers. The vinyl aromatic monomers can be styrene, alkyl substituted styrene, alpha-methylstyrene or alkyl substituted alpha-methylstyrene. The bead can be a copolymer such as a copolymer of styrene, $C_{1-6}$alkyl vinylbenzene and divinylbenzene. The bead can contain functional groups such as polyvinyl alcohol, hydroxy, nitro, halogen (e.g. bromo), cyano, aldehyde, or other groups that do not bind the sample. The bead can be unsubstituted or having bound thereto a hydrocarbon group having from 1 to 1,000,000 carbons. In one embodiment, the hydrocarbon group is an alkyl group having from 1 to 24 carbons. In another embodiment, the hydrocarbon group has from 1 to 8 carbons. In preferred embodiments, the bead is octadecyl modified poly(ethylvinylbenzene-divinylbenzene) or poly(styrene-divinylbenzene). The bead can also contain crosslinking-divinylmonomer such as divinyl benzene or butadiene.

In yet another embodiment, the invention is a method for separating a mixture of polynucleotides comprising flowing a mixture of polynucleotides having up to 1500 base pairs through a polymeric monolith, and separating the mixture of polynucleotides using MIPC. In this embodiment, the non-polar separation surfaces are the surfaces of interstitial spaces of a polymeric monolith. An example of such a monolith is a polymeric rod prepared within the confines of a chromatographic column. The monolith of the invention is characterized by having a DNA Separation Factor of at least 0.05. In a preferred embodiment, the monolith is characterized by having a DNA Separation Factor of at least 0.5. The monolith is preferably characterized by having a Mutation Separation Factor of at least 0.1. The mobile phase used in the separation preferably includes an organic solvent as exemplified by alcohol, nitrile, dimethylformamide, tetrahydrofuran, ester, ether, and mixtures thereof. Examples of suitable solvents include methanol, ethanol, 2-propanol, 1-propanol, tetrahydrofuran, ethyl acetate, acetonitrile, and mixtures thereof. The most preferred organic solvent is acetonitrile. The mobile phase preferably includes a counterion agent such as lower primary, secondary and tertiary amines, and lower trialkyammonium salts, or quaternary ammonium salts. More specifically, the counterion agent can be octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetrapropylammonium acetate, tetrabutylammonium acetate, and mixtures of any one or more of the above. The counterion agent includes an anion, e.g., acetate, carbonate, bicarbonate, phosphate, sulfate, nitrate, propionate, formate, chloride, perchlorate, and bromide. However, the most preferred counterion agent is triethylammonium acetate.

In the preferred embodiment, precautions are taken during the production of the polymeric monolith so that it is substantially free of multivalent cation contaminants and the monolith is treated, for example, by an acid wash treatment, to remove any residual surface metal contaminants. In one embodiment, the monolith is characterized by having a DNA Separation Factor of at least 0.05. In a preferred embodiment, the monolith is characterized by having a DNA Separation Factor of at least 0.5. Also in a preferred embodiment, the monolith is characterized by having a Mutation Separation Factor of at least 0.1.

In another aspect, the present invention is a method for treating the non-polar surface of a polymeric medium used for separating polynucleotides, such as the surface of beads in a MIPC column or the interstitial spaces in a polymeric monolith, in order to improve the resolution of polynucleotides, such as dsDNA, separated on said surface. This treatment includes contacting the surface with a solution containing a multivalent cation binding agent. In a preferred embodiment, the solution has a temperature of about 50° C. to 90° C. An example of this treatment includes flowing a solution containing a multivalent cation binding agent through a MIPC column, wherein the solution has a temperature of about 50° C. to 90° C. The preferred temperature is about 70° C. to 80° C. In a preferred embodiment, the multivalent cation binding agent is a coordination compound, examples of which include water-soluble chelating agents and crown ethers. Specific examples include acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, ethylenediaminetetraacetic acid (EDTA), metalphthalein, arsonic acids, α,α-bipyridine, 4-hydroxybenzothiazole, 8-hydroxyquinaldine, 8-hydroxyquinoline, 1,10-phenanthroline, picolinic acid, quinaldic acid, α,α',α"-terpyridyl, 9-methyl-2,3,7-trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyldithiocarbarbamate, and zinc dibenzyldithiocarbamate. However, the most preferred chelating agent is EDTA. In this aspect of the invention, the solution preferably includes an organic solvent as exemplified by alcohol, nitrile, dimethylformamide, tetrahydrofuran, ester, ether, and mixtures thereof. Examples of suitable solvents include methanol, ethanol, 2-propanol, 1-propanol, tetrahydrofuran, ethyl acetate, acetonitrile, and mixtures thereof. The most preferred organic solvent is acetonitrile. In one embodiment, the solution can include a counterion agent such as lower primary, secondary and tertiary amines, and lower trialkyammonium salts, or quaternary ammonium salts. More specifically, the counterion agent can be octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetrapropylammonium acetate, tetrabutylammonium acetate, and mixtures of any one or more of the above. The counterion agent includes an anion, e.g., acetate, carbonate, bicarbonate, phosphate, sulfate, nitrate, propionate, formate, chloride, perchlorate, and bromide. However, the most preferred counterion agent is triethylammonium acetate.

In yet a further aspect, the invention provides a method for storing a medium used for separating polynucleotides, e.g., the beads of a MIPC column or a polymeric monolith, in order to improve the resolution of double stranded DNA fragments separated using the medium. In the case of a MIPC column, the preferred method includes flowing a solution containing a multivalent cation binding agent through the column prior to storing the column. In a preferred embodiment, the multivalent cation binding agent is a coordination compound, examples of which include water-soluble chelating agents and crown ethers. Specific examples include acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, 8-hydroxyquinaldine, 8-hydroxyquinoline, 1,10-phenanthroline, picolinic acid, quinaldic acid, α,α',α"-terpyridyl, 9-methyl-2,3,7-trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyldithiocarbarbamate, and zinc dibenzyldithiocarbamate. However, the most preferred chelating agent is EDTA. In this aspect of the invention, the solution preferably includes an organic solvent as exemplified by alcohols, nitrites, dimethylformamide, tetrahydrofuran, esters, and ethers. The most preferred organic solvent is acetonitrile. The solution can also include a counterion agent such as lower primary, secondary and tertiary amines, and lower trialkyammonium salts, or quaternary ammonium salts. More specifically, the counterion agent can be octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetrapropylammonium acetate, tetrabutylammonium acetate, and mixtures of any one or more of the above. The counterion agent includes an anion, e.g., acetate, carbonate, bicarbonate, phosphate, sulfate, nitrate, propionate, formate, chloride, perchlorate, and bromide. However, the most preferred counterion agent is triethylammonium acetate.

BRIEF DESCRIPTION OF THE DRAWINGS

FIG. 1 is a schematic representation of how the DNA Separation Factor is measured.

FIG. 2 is a MIPC separation of pUC18 DNA-HaeIII digestion fragments on a column containing alkylated poly(styrene-divinylbenzene) beads. Peaks are labeled with the number of base pairs of the eluted fragment.

FIG. 3 is a MIPC separation of pUC18 DNA-HaeIII digestion fragments on a column containing nonporous 2.1 micron beads of underivatized poly(styrene-divinylbenzene).

FIG. 4 is a Van't Hoff plot of In k vs. 1/T [°K$^{-1}$] with alkylated poly(styrene-divinylbenzene) beads showing positive enthalpy using acetonitrile as the solvent.

FIG. 15 is a separation using alkylated beads and 25.0% THF as the solvent.

FIG. 16 is a combination isocratic/gradient separation on a non-alkylated poly(styrene-divinylbenzene) beads.

FIG. 21 is a DMIPC elution profile of a 100 bp PCR product from a wild-type strand of Lambda DNA.

FIG. 22 is a DMIPC elution profile of a hybridized mixture containing a Lambda DNA strand containing a mutation and wild type strand.

DETAILED DESCRIPTION OF THE INVENTION

Figure 5:
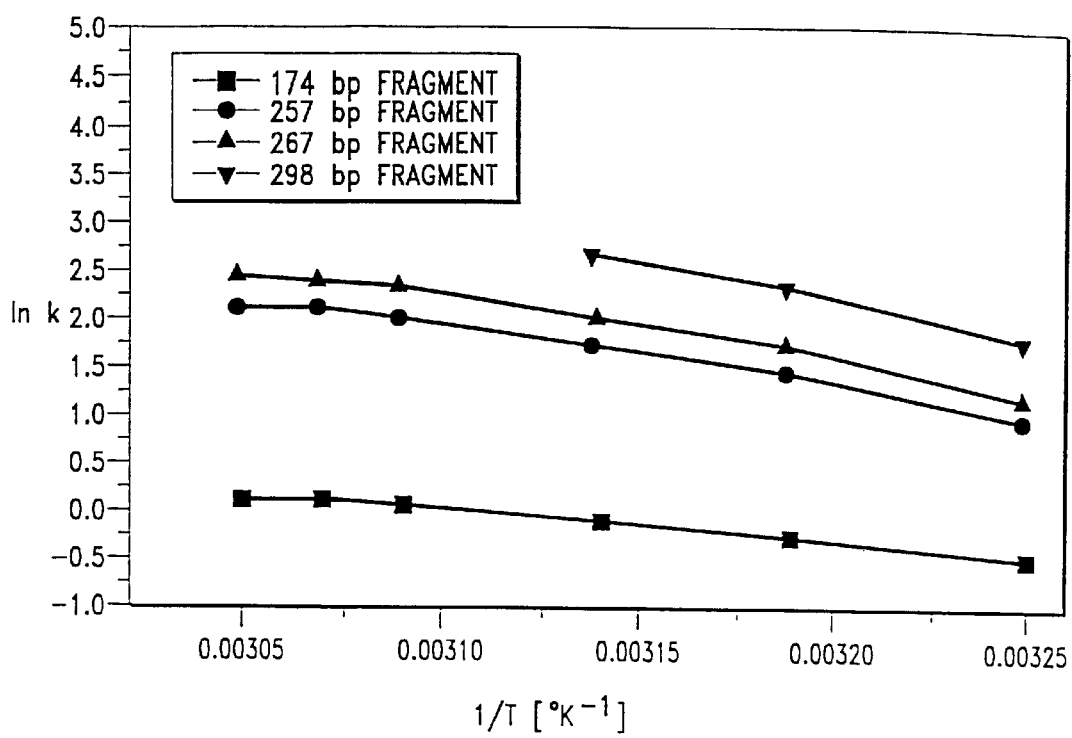
FIG. 5 is a Van't Hoff plot of In k vs. 1/T [°K$^{-1}$] with underivatized poly(styrene-divinylbenzene) beads showing positive enthalpy using acetonitrile as the solvent.

In its most general form, the subject matter of the present invention concerns the separation of polynucleotides. e.g. DNA, utilizing a stationary separation medium having non-polar surfaces. The preferred surfaces are essentially free from multivalent cation contamination which can trap polynucleotides. The separation is performed on the stationary surface. The surface can be porous, but preferably any surface pores are of a size which excludes the smallest polynucleotide being analyzed.

The medium can be enclosed in a column. In one embodiment, the non-polar surfaces comprise the surfaces of polymeric beads. In an alternative embodiment, the surfaces comprise the surfaces of interstitial spaces in a molded polymeric monolith. For purposes of simplifying the description of the invention and not by way of limitation, the separation of polynucleotides using nonporous beads, and the preparation of such beads, will be primarily described herein, it being understood that other separation surfaces, such as the interstitial surfaces of polymeric monoliths, are intended to be included within the scope of this invention. Monoliths such as rods contain polymer separation media which have been formed inside a column as a unitary structure having through pores or interstitial spaces which allow eluting solvent and analyte to pass through and which provide the non-polar separation surface.

In general, the only requirement for the separation media of the present invention is that they must have a surface that is either intrinsically non-polar or be bonded with a material that forms a surface having sufficient non-polarity to interact with a counterion agent.

In one aspect, the subject matter of the present invention is the separation of polynucleotides utilizing columns filled with nonporous polymeric beads having an average diameter of about 0.5–100 microns; preferably, 1–10 microns; more preferably, 1–5 microns. Beads having an average diameter of 1.0–3.0 microns are most preferred.

In U.S. Pat. No. 5,585,236, Bonn et al. had characterized the nucleic acid separation process as reverse phase ion pairing chromatography (RPIPC). However, since RPIPC does not incorporate certain essential characteristics described in the present invention, another term, Matched Ion Polynucleotide Chromatography (MIPC), has been selected. MIPC as used herein, is defined as a process for separating single and double stranded polynucleotides using non-polar beads, wherein the process uses a counterion agent, and an organic solvent to elute the nucleic acid from the beads, and wherein the beads are characterized as having a DNA Separation Factor of at least 0.05. In a preferred embodiment, the beads have a DNA Separation Factor of at least 0.5. In an optimal embodiment, the beads have a DNA Separation Factor of at least 0.95.

The performance of the beads of the present invention is demonstrated by high efficiency separation by MIPC of double stranded and single stranded DNA. Applicants have found that a useful criterion for measuring performance of the beads is a DNA Separation Factor. This is measured as the resolution of 257- and 267-base pair double stranded DNA fragments of a pUC18 DNA-HaeIII restriction digest and is defined as the ratio of the distance from the valley between the peaks to the top of the peaks, over the distance from the baseline to the top of the peaks. Referring to the schematic representation of FIG. 1, the DNA Separation Factor is determined by measuring the distance "a" from the baseline to the valley "e" between the peaks "b" and "c" and the distance "d" from the valley "e" to the top of one of the peaks "b" or "c". If the peak heights are unequal, the highest peak is used to obtain "d." The DNA Separation Factor is the ratio of d/(a+d). The peaks of 257- and 267-base pairs in this schematic representation are similar in height. Operational beads of the present invention have a DNA Separation Factor of at least 0.05. Preferred beads have a DNA Separation Factor of at least 0.5.

Without wishing to be bound by theory, Applicants believe that the beads which conform to the DNA Separation Factor as specified herein have a pore size which essentially excludes the polynucleotides being separated from entering the bead. As used herein, the term "nonporous" is defined to denote a bead which has surface pores having a diameter that is less than the size and shape of the smallest DNA fragment in the separation in the solvent medium used therein. Included in this definition are polymer beads having these specified maximum size restrictions in their natural state or which have been treated to reduce their pore size to meet the maximum effective pore size required. Preferably, all beads which provide a DNA Separation Factor of at least 0.5 are intended to be included within the definition of "nonporous" beads.

The surface conformations of nonporous beads of the present invention can include depressions and shallow pit-like structures which do not interfere with the separation process. A pretreatment of a porous bead to render it nonporous can be effected with any material which will fill the pores in the bead structure and which does not significantly interfere with the MIPC process.

Pores are open structures through which mobile phase and other materials can enter the bead structure. Pores are often interconnected so that fluid entering one pore can exit from another pore. Applicants believe that pores having dimensions that allow movement of the polynucleotide into the interconnected pore structure and into the bead impair the resolution of separations or result in separations that have very long retention times. In MIPC, however, the beads are "nonporous" and the polynucleotides do not enter the bead structure.

The term polynucleotide is defined as a linear polymer containing an indefinite number of nucleotides, linked from one ribose (or deoxyribose) to another via phosphoric residues. The present invention can be used in the separation of RNA or of double- or single-stranded DNA. For purposes of simplifying the description of the invention, and not by way of limitation, the separation of double-stranded DNA will be described in the examples herein, it being understood that all polynucleotides are intended to be included within the scope of this invention.

Chromatographic efficiency of the column beads is predominantly influenced by the properties of surface and near-surface areas. For this reason, the following descriptions are related specifically to the close-to-the-surface region of the polymeric beads. The main body and/or the center of such beads can exhibit entirely different chemistries and sets of physical properties from those observed at or near the surface of the polymeric beads of the present invention.

In another embodiment of the present invention, the separation medium can be in the form of a polymeric monolith such as a rod-like monolithic column. The monolithic column is polymerized or formed as a single unit inside of a tube as described in the Examples hereinbelow. The through pore or interstitial spaces provide for the passage of eluting solvent and analyte materials. The separation is performed on the stationary surface. The surface can be porous, but is preferably nonporous. The form and function of the separations are identical to columns packed with beads. As with beads, the pores contained in the rod must be compatible with DNA and not trap the material. Also, the rod must not contain contamination that will trap DNA.

The molded polymeric rod of the present invention is prepared by bulk free radical polymerization within the confines of a chromatographic column. The base polymer of the rod can be produced from a variety of polymerizable monomers. For example, the monolithic rod can be made from polymers, including mono- and di-vinyl substituted aromatic compounds such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly (glycidyl methacrylate-co-ethylene dimethacrylate), poly (styrene-divinylbenzene) and poly(ethylvinylbenzene-divinylbenzene. The rod can be unsubsituted or substituted with a substituent such as a hydrocarbon alkyl or an aryl group. The alkyl group optionally has 1 to 1,000,000 carbons inclusive in a straight or branched chain, and includes straight chained, branch chained, cyclic, saturated, unsaturated nonionic functional groups of various types including aldehyde, ketone, ester, ether, alkyl groups, and the like, and the aryl groups includes as monocyclic, bicyclic, and tricyclic aromatic hydrocarbon groups including phenyl, naphthyl, and the like. In a preferred embodiment, the alkyl group has 1–24 carbons. In a more preferred embodiment, the alkyl group has 1–8 carbons. The substitution can also contain hydroxy, cyano, nitro groups, or the like which are considered to be non-polar, reverse phase functional groups. Methods for hydrocarbon substitution are conventional and well-known in the art and are not an aspect of this invention. The preparation of polymeric monoliths is by conventional methods well known in the art as described in the following references: Wang et al. (*J. Chromatog. A* 699:230 (1994)), Petro et al. (*Ana. Chem.* 68:315 (1996)), and the following U.S. Pat. Nos. 5,334,310; 5,453,185; 5,522,994 (to Frechet). Monolith or rod columns are commercially available form Merck & Co (Darmstadt, Germany).

The nonporous polymeric beads of the present invention are prepared by a two-step process in which small seed beads are initially produced by emulsion polymerization of suitable polymerizable monomers. The emulsion polymerization procedure of the invention is a modification of the procedure of Goodwin, et al. (*Colloid & Polymer Sci.,* 252:464–471 (1974)). Monomers which can be used in the emulsion polymerization process to produce the seed beads include styrene, alkyl substituted styrenes, alpha-methyl styrene, and alkyl substituted alpha-methyl styrene. The seed beads are then enlarged and, optionally, modified by substitution with various groups to produce the nonporous polymeric beads of the present invention.

The seed beads produced by emulsion polymerization can be enlarged by any known process for increasing the size of the polymer beads. For example, polymer beads can be enlarged by the activated swelling process disclosed in U.S. Pat. No. 4,563,510. The enlarged or swollen polymer beads are further swollen with a crosslinking polymerizable monomer and a polymerization initiator. Polymerization increases the crosslinking density of the enlarged polymeric bead and reduces the surface porosity of the bead. Suitable crosslinking monomers contain at least two carbon-carbon double bonds capable of polymerization in the presence of an initiator. Preferred crosslinking monomers are divinyl monomers, preferably alkyl and aryl (phenyl, naphthyl, etc.) divinyl monomers and include divinyl benzene, butadiene, etc. Activated swelling of the polymeric seed beads is useful to produce polymer beads having an average diameter ranging from 1 up to about 100 microns.

Alternatively, the polymer seed beads can be enlarged simply by heating the seed latex resulting from emulsion polymerization. This alternative eliminates the need for activated swelling of the seed beads with an activating solvent. Instead, the seed latex is mixed with the crosslinking monomer and polymerization initiator described above, together with or without a water-miscible solvent for the crosslinking monomer. Suitable solvents include acetone, tetrahydrofuran (THF), methanol, and dioxane. The resulting mixture is heated for about 1–12 hours, preferably about 4–8 hours, at a temperature below the initiation temperature of the polymerization initiator, generally, about 10° C.–80° C., preferably 30° C.–60° C. Optionally, the temperature of the mixture can be increased by 10–20% and the mixture heated for an additional 1 to 4 hours. The ratio of monomer to polymerization initiator is at least 100:1, preferably about 100:1 to about 500:1, more preferably about 200:1 in order to ensure a degree of polymerization of at least 200. Beads having this degree of polymerization are sufficiently pressure-stable to be used in high pressure liquid chromatography (HPLC) applications. This thermal swelling process allows one to increase the size of the bead by about 110–160% to obtain polymer beads having an average diameter up to about 5 microns, preferably about 2–3 microns. The thermal swelling procedure can, therefore, be used to produce smaller particle sizes previously accessible only by the activated swelling procedure.

Following thermal enlargement, excess crosslinking monomer is removed and the particles are polymerized by exposure to ultraviolet light or heat. Polymerization can be conducted, for example, by heating of the enlarged particles to the activation temperature of the polymerization initiator and continuing polymerization until the desired degree of polymerization has been achieved. Continued heating and polymerization allows one to obtain beads having a degree of polymerization greater than 500.

In the present invention, the packing material disclosed by Bonn et al. or U.S. Pat. No. 4,563,510 can be modified through substitution of the polymeric beads with alkyl groups or can be used in its unmodified state. For example, the polymer beads can be alkylated with 1 or 2 carbon atoms by contacting the beads with an alkylating agent, such as methyl iodide or ethyl iodide. Alkylation is achieved by mixing the polymer beads with the alkyl halide in the presence of a Friedel-Crafts catalyst to effect electrophilic aromatic substitution on the aromatic rings at the surface of the polymer blend. Suitable Friedel-Crafts catalysts are well-known in the art and include Lewis acids such as aluminum chloride, boron trifluoride, tin tetrachloride, etc. The beads can be hydrocarbon substituted by substituting the corresponding hydrocarbon halide for methyl iodide in the above procedure, for example.

The term alkyl as used herein in reference to the beads of the present invention is defined to include alkyl and alkyl substituted aryl groups, having from 1 to 1,000,000 carbons, the alkyl groups including straight chained, branch chained, cyclic, saturated, unsaturated nonionic functional groups of various types including aldehyde, ketone, ester, ether, alkyl groups, and the like, and the aryl groups including as monocyclic, bicyclic, and tricyclic aromatic hydrocarbon groups including phenyl, naphthyl, and the like. Methods for alkyl substitution are conventional and well-known in the art and are not an aspect of this invention. The substitution can also contain hydroxy, cyano, nitro groups, or the like which are considered to be non-polar, reverse phase functional groups.

The chromatographic material reported in the Bonn patent was limited to nonporous beads substituted with alkyl groups having at least 3 carbons because Bonn et al. were unsuccessful in obtaining separations using polymer beads lacking this substitution. Additionally, the polymer beads were limited to a small group of vinyl aromatic monomers, and Bonn et al. were unable to effect double stranded DNA separations with other materials.

In the present invention, it has now been surprisingly discovered that successful separation of double stranded DNA can be achieved using underivatized nonporous beads as well as using beads derivatized with alkyl groups having 1 to 1,000,000 carbons.

The base polymer of the invention can also be other polymers, non-limiting examples of which include mono- and di-vinyl substituted aromatics such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly(styrene-divinylbenzene) and poly (ethylvinylbenzene-divinylbenzene). Methods for making beads from these polymers are conventional and well known in the art (for example, see U.S. Pat. No. 4,906,378). The physical properties of the surface and near-surface areas of the beads are the predominant influence on chromatographic efficiency. The polymer, whether derivatized or not, must provide a nonporous, non-reactive, and non-polar surface for the MIPC separation.

In an important aspect of the present invention, the beads and other media of the invention are characterized by having low amounts of metal contaminants or other contaminants that can bind DNA. The preferred beads of the present invention are characterized by having been subjected to precautions during production, including a decontamination treatment, such as an acid wash treatment, designed to substantially eliminate any multivalent cation contaminants (e.g. Fe(III), Cr(III), or colloidal metal contaminants). Only very pure, non-metal containing materials should be used in the production of the beads in order that the resulting beads will have minimum metal content.

In addition to the beads themselves being substantially metal-free, Applicants have also found that, to achieve optimum peak separation during MIPC, the separation column and all process solutions held within the column or flowing through the column are preferably substantially free of multivalent cation contaminants. As described in commonly owned U.S. Pat. No. 5,772,889 to Gjerde (1998), and in co-pending U.S. patent applications Ser. No. 09/081,040 (filed May 18, 1998) and Ser. No. 09/080,547 (filed May 18, 1998) this can be achieved by supplying and feeding solutions that enter the separation column with components which have process solution-contacting surfaces made of material which does not release multivalent cations into the process solutions held within or flowing through the column, in order to protect the column from multivalent cation contamination. The process solution-contacting surfaces of the system components are preferably material selected from the group consisting of titanium, coated stainless steel, passivated stainless steel, and organic polymer.

There are two places where multivalent cation binding agents, e.g., chelators, are used in MIPC separations. In one embodiment, these binding agents can be incorporated into a solid through which the mobile phase passes. Contaminants are trapped before they reach places within the system that can harm the separation. In these cases, the functional group is attached to a solid matrix or resin (e.g., a flow-through cartridge, usually an organic polymer, but sometimes silica or other material). The capacity of the matrix is preferably about 2 mequiv./g. An example of a suitable chelating resin is available under the trademark CHELEX 100 (Dow Chemical Co.) containing an iminodiacetate functional group.

In another embodiment, the multivalent cation binding agent can be added to the mobile phase. The binding functional group is incorporated into an organic chemical structure. The preferred multivalent cation binding agent fulfills three requirements. First, it is soluble in the mobile phase. Second, the complex with the metal is soluble in the mobile phase. Multivalent cation binding agents such as EDTA fulfill this requirement because both the chelator and the multivalent cation binding agent-metal complex contain charges which make them both water-soluble. Also, neither precipitate when acetonitrile, for example, is added. The solubility in aqueous mobile phase can be enhanced by attaching covalently bound ionic functionality, such as, sulfate, carboxylate, or hydroxy. A preferred multivalent cation binding agent can be easily removed from the column by washing with water, organic solvent or mobile phase. Third, the binding agent must not interfere with the chromatographic process.

The multivalent cation binding agent can be a coordination compound. Examples of preferred coordination compounds include water soluble chelating agents and crown ethers. Non-limiting examples of multivalent cation binding agents which can be used in the present invention include acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, 8-hydroxyquinaldine, 8-hydroxyquinoline, 1,10-phenanthroline, picolinic acid, quinaldic acid, α,α',α"-terpyridyl, 9-methyl-2,3,7-trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyldithiocarbarbamate, and zinc dibenzyldithiocarbamate. These and other examples are described by Perrin in *Organic Complexing Reagents: Structure, Behavior, and Application to Inorganic Analysis*, Robert E. Krieger Publishing Co. (1964). In the present invention, a preferred multivalent cation binding agent is EDTA.

To achieve high resolution chromatographic separations of polynucleotides, it is generally necessary to tightly pack the chromatographic column with the solid phase polymer beads. Any known method of packing the column with a column packing material can be used in the present invention to obtain adequate high resolution separations. Typically, a slurry of the polymer beads is prepared using a solvent having a density equal to or less than the density of the polymer beads. The column is then filled with the polymer bead slurry and vibrated or agitated to improve the packing density of the polymer beads in the column. Mechanical vibration or sonication are typically used to improve packing density.

For example, to pack a 50×4.6 mm I.D. column, 2.0 grams of beads can be suspended in 10 mL of methanol with the aid of sonication. The suspension is then packed into the column using 50 mL of methanol at 8,000 psi of pressure. This improves the density of the packed bed.

The separation method of the invention is generally applicable to the chromatographic separation of single stranded and double stranded polynucleotides of DNA and RNA. Samples containing mixtures of polynucleotides can result from total synthesis of polynucleotides, cleavage of DNA or RNA with restriction endonucleases or with other enzymes or chemicals, as well as nucleic acid samples which have been multiplied and amplified using polymerase chain reaction techniques.

The method of the present invention can be used to separate double stranded polynucleotides having up to about 1500 to 2000 base pairs. In many cases, the method is used to separate polynucleotides having up to 600 bases or base pairs, or which have up to 5 to 80 bases or base pairs.

In a preferred embodiment, the separation is by Matched Ion Polynucleotide Chromatography (MIPC). The nonporous beads of the invention are used as a reverse phase material that will function with counterion agents and a solvent gradient to effect the DNA separations. In MIPC, the polynucleotides are paired with a counterion and then subjected to reverse phase chromatography using the nonporous beads of the present invention.

There are several types of counterions suitable for use with MIPC. These include a mono-, di-, or trialkylamine that can be protonated to form a positive counter charge or a quaternary alkyl substituted amine that already contains a positive counter charge. The alkyl substitutions may be uniform (for example, triethylammonium acetate or tetrapropylammonium acetate) or mixed (for example, propyldiethylammonium acetate). The size of the alkyl group may be small (methyl) or large (up to 30 carbons) especially if only one of the substituted alkyl groups is large and the others are small. For example octyldimethylammonium acetate is a suitable counterion agent. Preferred counterion agents are those containing alkyl groups from the ethyl, propyl or butyl size range.

The purpose of the alkyl group is to impart a nonpolar character to the polynucleic acid through a matched ion process so that the polynucleic acid can interact with the nonpolar surface of the separation media. The requirements for the extent of nonpolarity of the counterion-DNA pair depends on the polarity of the separation media, the solvent conditions required for separation, the particular size and type of fragment being separated. For example, if the polarity of the separation media is increased, then the polarity of the counterion agent may have to change to match the polarity of the surface and increase interaction of the counterion-DNA pair. Triethylammonium acetate is preferred although quaternary ammonium reagents such as tetrapropyl or tetrabutyl ammonium salts can be used when extra nonpolar character is needed or desired. In general, as the polarity of the alkyl group is increased, size specific separations, sequence independent separations become more possible. Quaternary counterion reagents are not volatile, making collection of fragments more difficult.

In some cases, it may be desired to increase the range of concentration of organic solvent used to perform the separation. For example, increasing the alkyl length on the counterion agent will increase the nonpolarity of the counterion-DNA pair resulting in the need to either increase the concentration of the mobile phase organic solvent, or increase the strength of the organic solvent type, e.g. acetonitrile is about two times more effective than methanol for eluting polynucleic acids. There is a positive correlation between concentration of the organic solvent required to elute a fragment from the column and the length of the fragment. However, at high organic solvent concentrations, the polynucleotide could precipitate. To avoid precipitation, a strong organic solvent or a smaller counterion alkyl group can be used. The alkyl group on the counterion reagent can also be substituted with halides, nitro groups, or the like to moderate polarity.

The mobile phase preferably contains a counterion agent. Typical counterion agents include trialkylammonium salts of organic or inorganic acids, such as lower alkyl primary, secondary, and lower tertiary amines, lower trialkyammonium salts and lower quaternary alkyalmmonium salts. Lower alkyl refers to an alkyl radical of one to six carbon atoms, as exemplified by methyl, ethyl, n-butyl, i-butyl, t-butyl, isoamyl, n-pentyl, and isopentyl. Examples of counterion agents include octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetrapropylammonium acetate, and tetrabutylammonium acetate. Although the anion in the above examples is acetate, other anions may also be used, including carbonate, phosphate, sulfate, nitrate, propionate, formate, chloride, and bromide, or any combination of cation and anion. These and other agents are described by Gjerde, et al. in *Ion Chromatography*, 2nd Ed., Dr. Alfred H üthig Verlag Heidelberg (1987). Counterion agents that are volatile are preferred for use in the method of the invention, with triethylammonium acetate (TEAA) and triethylammonium hexafluoroisopropyl alcohol being most preferred.

To achieve optimum peak resolution during the separation of DNA by MIPC using the beads of the invention, the method is preferably performed at a temperature within the range of 20° C. to 90° C.; more preferably, 30° C. to 80° C.; most preferably, 50° C. to 75° C. The flow rate is selected to yield a back pressure not exceeding 5000 psi. In general, separation of single-stranded fragments should be performed at higher temperatures.

Applicants have found that the temperature at which the separation is performed affects the choice of organic solvents used in the separation. One reason is that the solvents affect the temperature at which a double stranded DNA will melt to form two single strands or a partially melted complex of single and double stranded DNA. Some solvents can stabilize the melted structure better than other solvents. The other reason a solvent is important is because it affects the distribution of the DNA between the mobile phase and the stationary phase. Acetonitrile and 1-propanol are preferred solvents in these cases. Finally, the toxicity (and cost) of the solvent can be important. In this case, methanol is preferred over acetonitrile and 1-propanol is preferred over methanol.

When the separation is performed at a temperature within the above range, an organic solvent that is water soluble is preferably used, for example, alcohols, nitriles, dimethylformamide (DMF), tetrahydrofuran (THF), esters, and ethers. Water soluble solvents are defined as those which exist as a single phase with aqueous systems under all conditions of operation of the present invention. Solvents which are particularly preferred for use in the method of this invention include methanol, ethanol, 2-propanol, 1-propanol, tetrahydrofuran (THF), and acetonitrile, with acetonitrile being most preferred overall.

Mixtures of polynucleotides in general, and double stranded DNA in particular, are effectively separated using Matched Ion Polynucleotide Chromatography (MIPC). MIPC separations of polynucleotides at non-denaturing temperature, typically less than about 50° C., are based on base pair length. However, even traces of multivalent cations anywhere in the solvent flow path can cause a significant deterioration in the resolution of the separation after multiple uses of an MIPC column. This can result in increased cost caused by the need to purchase replacement columns and increased downtime.

Therefore, effective measures are preferably taken to prevent multivalent metal cation contamination of the separation system components, including separation media and mobile phase contacting. These measures include, but are not limited to, washing protocols to remove traces of multivalent cations from the separation media and installation of guard cartridges containing cation capture resins, in line between the mobile phase reservoir and the MIPC column. These, and similar measures, taken to prevent system contamination with multivalent cations have resulted in extended column life and reduced analysis downtime.

Recently, MIPC has been successfully applied to the detection of mutations in double stranded DNA by separating heteroduplexes from homoduplexes as described in co-pending U.S. patent application Ser. No. 09/129,105 filed Aug. 4, 1998 which is herein incorporated by reference. Such separations depend on the lower temperature required to denature a heteroduplex at the site of base pair mismatch compared to a fully complimentary homoduplex DNA fragment. MIPC, when performed at a temperature which is sufficient to partially denature a heteroduplex is referred to herein as Denaturing Matched Ion Polynucleotide Chromatography (DMIPC). DMIPC is typically performed at a temperature between 52° C. and 70° C. The optimum temperature for performing DMIPC is 54° C. to 59° C.

The previously described precautions taken to remove multivalent metal cations were adequate for maintaining column life, as demonstrated by good separation efficiency, under non-denaturing conditions. However, Applicants have surprisingly found that when performed at partially denaturing temperature, conditions for effective DMIPC separations become more stringent. For example, a separation of a standard pUC18 HaeIII digest on a MIPC column at 50° C. provided a good separation of all the DNA fragments in the digest. However, a standard 209 bp DYS271 mutation detection mixture of homoduplexes and heteroduplexes, prepared as described in Example 15, applied to the same MIPC column and eluted under DMIPC. conditions, i.e., 56° C., afforded a poor separation the mixture components. In order to optimize column life and maintain effective separation performance of homoduplexes from heteroduplexes at partially denaturing temperatures, as is required for mutation detection, special column washing and storage procedures are used in the embodiments of the invention as described hereinbelow.

In one aspect of this invention, therefore, an aqueous solution of multivalent cation binding agent is flowed through the column to maintain separation efficiency. In order to maintain the separation efficiency of a MIPC column, the column is preferably washed with multivalent cation binding agent solution after about 500 uses or when the performance starts to degrade. Examples of suitable cation binding agents are as described hereinabove.

The concentration of a solution of the cation binding agent can be between 0.01 M and 1 M. In a preferred embodiment, the column washing solution contains EDTA at a concentration of about 0.03 to 0.1 M.

In another embodiment, the solution contains an organic solvent selected from the group consisting of acetonitrile, ethanol, methanol, 2-propanol, and ethyl acetate. A preferred solution contains at least 2% organic solvent to prevent microbial growth. In a most preferred embodiment a solution containing 25% acetonitrile is used to wash a MIPC column. The multivalent cation binding solution can contain a counterion agent as described hereinabove.

In one embodiment of a column washing procedure, the MIPC separation column is washed with the multivalent cation binding solution at an elevated temperature in the range of 50° C. to 80° C. In a preferred embodiment the column is washed with a solution containing EDTA, TEAA, and acetonitrile, in the 70° C. to 80° C. temperature range. In a specific embodiment, the solution contains 0.032 M EDTA, 0.1 M TEAA, and 25% acetonitrile.

Column washing can range from 30 seconds to one hour. For example, in a high throughput DMIPC assay, the column can be washed for 30 seconds after each sample, followed by equilibration with mobile phase. Since DMIPC can be automated by computer, the column washing procedure can be incorporated into the mobile phase selection program without additional operator involvement. In a preferred procedure, the column is washed with multivalent cation binding agent for 30 to 60 minutes at a flow rate preferably in the range of about 0.05 to 1.0 mL/min.

In one embodiment, a DMIPC column is tested with a standard mutation detection mixture of homoduplexes and heteroduplexes after about 1000 sample analyses. If the separation of the standard mixture has deteriorated compared to a freshly washed column, then the column can be washed for 30 to 60 minutes with the multivalent cation binding solution at a temperature above about 50° C. to restore separation performance.

Applicants have found that other treatments for washing a column can also be used alone or in combination with those indicated hereinabove. These include: use of high pH washing solutions (e.g., pH 10–12), use of denaturants such as urea or formamide, and reverse flushing the column with washing solution.

In another aspect, Applicants have discovered that column separation efficiency can be preserved by storing the column separation media in the column containing a solution of multivalent cation binding agent therein. The solution of binding agent may also contain a counterion agent. Any of the multivalent cation binding agents, counterion agents, and solvents described hereinabove are suitable for the purpose of storing a MIPC column. In a preferred embodiment, a column packed with MIPC separation media is stored in an organic solvent containing a multivalent cation binding agent and a counterion agent. An example of this preferred embodiment is 0.032 M EDTA and 0.1 M TEAA in 25% aqueous acetonitrile. In preparation for storage, a solution of multivalent cation binding agent, as described above, is passed through the column for about 30 minutes. The column is then disconnected from the HPLC apparatus and the column ends are capped with commercially available threaded end caps made of material which does not release multivalent cations. Such end caps can be made of coated stainless steel, titanium, organic polymer or any combination thereof.

Figure 20:
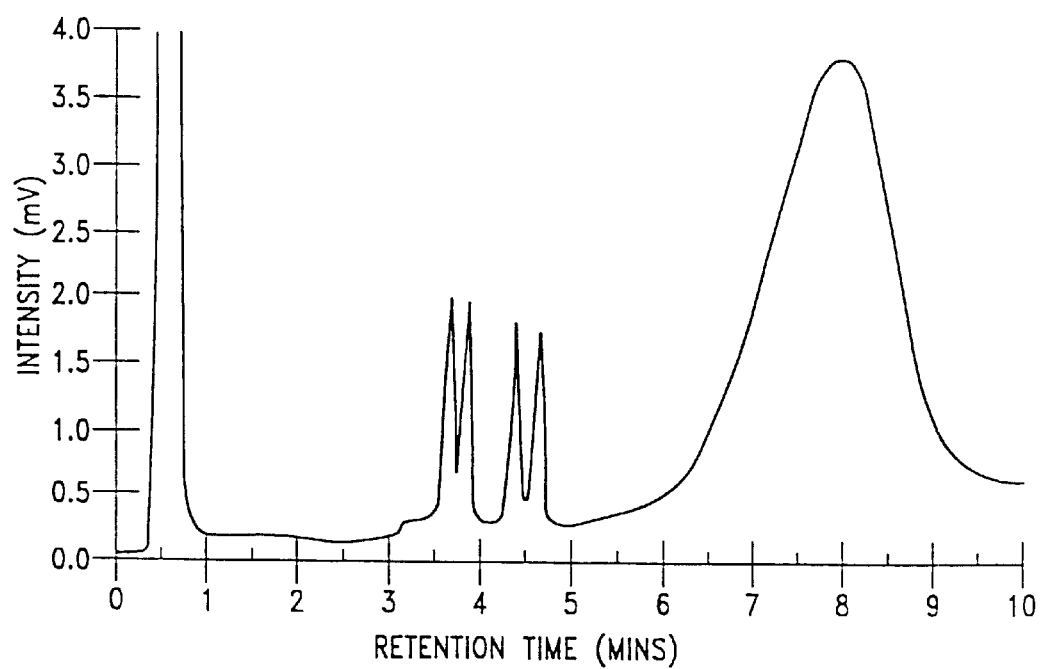
FIG. 20 is an elution profile of another injection of the same 209 bp mixture and using the same column as in FIG. 19, but after flushing the column with 0.1 M TEAA, 25% acetonitrile, and 0.32 M EDTA for 45 minutes at 75° C.
Figure 18:
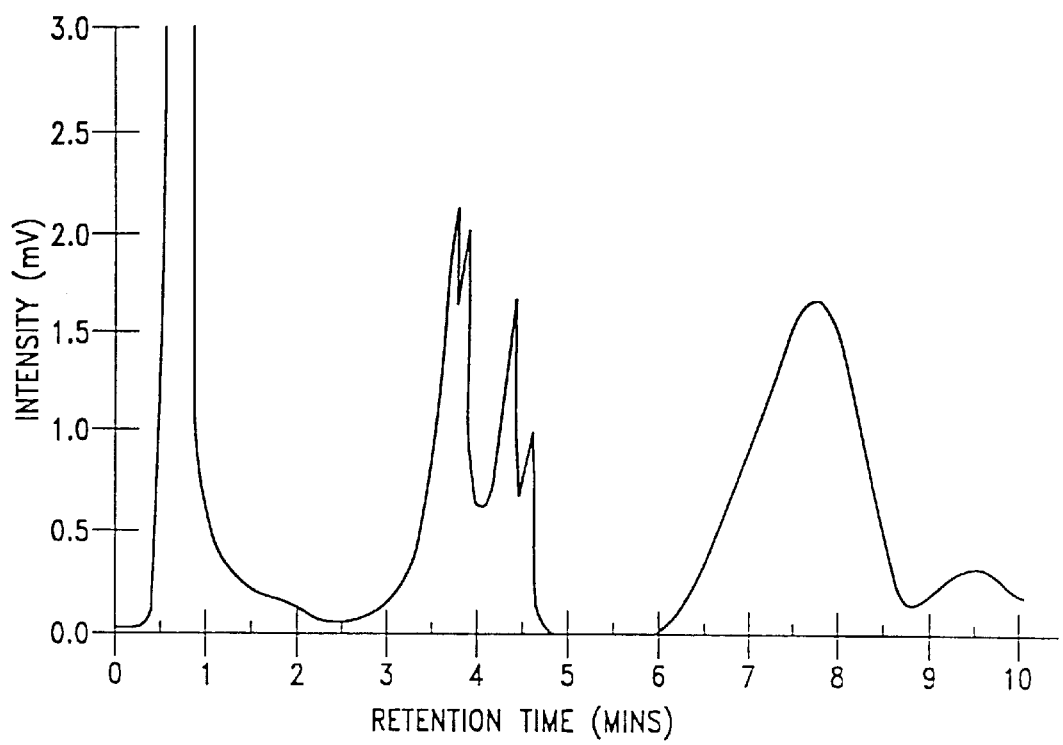
FIG. 18 is an elution profile showing separation of a 209 base pair homoduplex/heteroduplex mutation detection mixture performed by DMIPC at 56° C.
Figure 19:
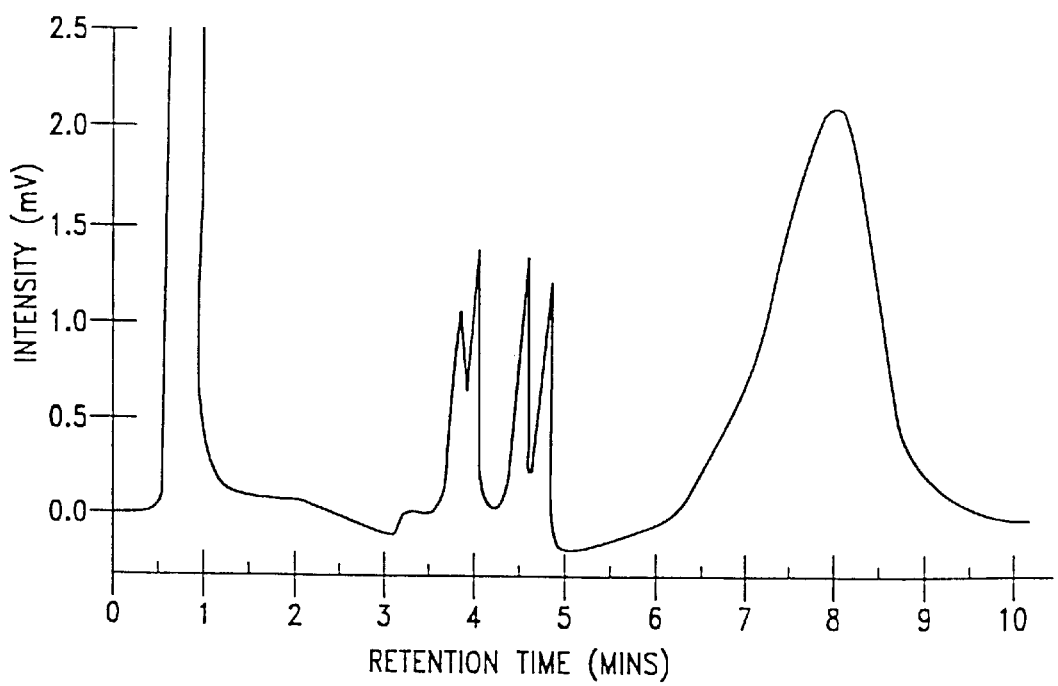
FIG. 19 is an elution profile of another injection of the same 209 bp mixture and using the same column as in FIG. 18, but after changing the guard cartridge and replacing the pump-valve filter.

The effectiveness of the surprising discovery made by Applicants, that washing a MIPC column with a multivalent cation binding agent restores the ability of the column to separate heteroduplexes and homoduplexes in mutation detection protocols under DMIPC conditions, is described in Example 14 and demonstrated in FIGS. 18, 19, and 20. As described in Example 14, Applicants noticed a decrease in resolution of homoduplexes and heteroduplexes during the use of a MIPC column in mutation detection. However, no apparent degradation in resolution was observed when a DNA standard containing pUC18 HaeIII digest (Sigma/Aldrich Chemical Co.) was applied at 50° C. (not shown). In order to further test the column performance, a mixture of homoduplexes and heteroduplexes in a 209 bp DNA standard was applied to the column under DMIPC conditions of 56° C. (Kuklin et al., *Genetic Testing* 1:201 (1998). It was surprisingly observed the peaks representing the homoduplexes and heteroduplexes of the mutation detection standard were poorly resolved (FIG. 18).

FIG. 19 shows some improvement in the separation of homoduplexes and heteroduplexes of the standard mutation detection mixture when a guard cartridge containing cation capture resin was deployed in line between the solvent reservoir and the MIPC system. The chromatography shown in FIG. 19 was performed at 56° C. The column used in FIG. 19 was the same column used in the separation shown in FIG. 18 and for separating the standard pUC18 HaeIII digest.

FIG. 20 shows the separation of homoduplexes and heteroduplexes of the standard mutation detection mixture at 56° C. on the same column used to generate the chromatograms in FIGS. 18 and 19. However, in FIG. 20 the column was washed for 45 minutes with a solution comprising 32 mM EDTA and 0.1 M TEAA in 25% acetonitrile at 75° C. prior to sample application. FIG. 20 shows four cleanly resolved peaks representing the two homoduplexes and the two heteroduplexes of the standard 209 bp mutation detection mixture. This restoration of the separation ability, after washing with a solution containing a cation binding agent, of the MIPC column under DMIPC conditions compared to the chromatograms of FIGS. 18 and 19 clearly shows the effectiveness and the utility of the present invention.

In an important aspect of the present invention, Applicants have developed a standardized criteria to evaluate the performance of a DMIPC separation media. DMIPC as used herein, is defined as a process for separating heteroduplexes and homoduplexes using a non-polar separation medium (e.g., beads or rod) in the column, wherein the process uses a counterion agent, and an organic solvent to desorb the nucleic acid from the medium, and wherein the medium is characterized as having a Mutation Separation Factor (MSF) of at least 0.1. In one embodiment, the medium has a Mutation Separation Factor of at least 0.2. In a preferred embodiment, the medium has a Mutation Separation Factor of at least 0.5. In an optimal embodiment, the medium has a Mutation Separation Factor of at least 1.0.

The performance of the column is demonstrated by high efficiency separation by DMIPC of heteroduplexes and homoduplexes. Applicants have found that the best criterion for measuring performance is a Mutation Separation Factor as described in Example 13. This is measured as the difference between the areas of the resolved heteroduplex and homoduplex peaks. A correction factor may be applied to the generated areas underneath the peaks. The following aspects may affect the calculated areas of the peaks and reproducibility of the same: baseline drawn, peak normalization, inconsistent temperature control, inconsistent elution conditions, detector instability, flow rate instability, inconsistent PCR conditions, and standard and sample degradation. Some of these aspects are discussed by Snyder, et al., in *Introduction to Modern Liquid Chromatography, $2^{nd}$ Ed.*, John Wiley and Sons, pp. 542–574 (1979) which is incorporated by reference herein.

The Mutation Separation Factor (MSF) is determined by the following equation:

MSF=(area peak 2–area peak 1)/area peak 1 where area peak 1 is the area of the peak measured after DMIPC analysis of wild type and area peak 2 is the total area of the peak or peaks measured after DMIPC analysis of a hybridized mixture containing a putative mutation, with the hereinabove correction factors taken into consideration, and where the peak heights have been normalized to the wild type peak height. Separation particles are packed in an HPLC column and tested for their ability to separate a standard hybridized mixture containing a wild type 100 bp Lambda DNA fragment and the corresponding 100 bp fragment containing an A to C mutation at position 51.

High pressure pumps are used for pumping mobile phase in the systems described in U.S. Pat. No. 5,585,236 to Bonn and in U.S. Pat. No. 5,772,889 to Gjerde. It will be appreciated that other methods are known for driving mobile phase through separation media and can be used in carrying out the separations of polynucleotides as described in the present invention. A non-limiting example of such an alternative method includes "capillary electrochromatography" (CEC) in which an electric field is applied across capillary columns packed with microparticles and the resulting electroosmotic flow acts as a pump for chromatography. Electroosmosis is the flow of liquid, in contact with a solid surface, under the influence of a tangentially applied electric field. The technique combines the advantages of the high efficiency obtained with capillary electrophoretic separations, such as capillary zone electrophoresis, and the general applicability of HPLC. CEC has the capability to drive the mobile phase through columns packed with chromatographic particles, especially small particles, when using electroosmotic flow. High efficiencies can be obtained as a result of the plug-like flow profile. In the use of CEC in the present invention, solvent gradients are used and rapid separations can be obtained using high electric fields. The following references describing CEC are each incorporated in their entirety herein: Dadoo, et al, *LC-GC* 15:630 (1997); Jorgenson, et al., *J. Chromatog.* 218:209 (1981); Pretorius, et al., *J. Chromatog.* 99:23 (1974); and the following U.S. patent Nos. to Dadoo U.S. Pat. Nos. 5,378,334 (1995), 5,342,492 (1994), and 5,310,463 (1994). In the operation of this aspect of the present invention, the capillaries are packed, either electrokinetically or using a pump, with the separation beads described in the present specification. In another embodiment, a polymeric rod is prepared by bulk free radical polymerization within the confines of a capillary column. Capillaries are preferably formed from fused silica tubing or etched into a block. The packed capillary (e.g., a 150-μm i.d. with a 20-cm packed length and a window located immediately before the outlet frit) is fitted with frits at the inlet and outlet ends. An electric field, e.g., 2800 V/cm, is applied. Detection can be by uv absorbance or by fluorescence. A gradient of organic solvent, e.g., acetonitrile, is applied in a mobile phase containing counterion agent (e.g. 0.1 M TEAA). to elute the polynucleotides. The column temperature is maintained by conventional temperature control means. In the preferred embodiment, all of the precautions for minimizing trace metal contaminants as described hereinabove are employed in using CEC.

In a related method, mixtures of polynucleotides are separated on thin layer chromatography (TLC) plates. In this method, the beads of the present invention are mixed with a binder and bound to a TLC plate by conventional methods (Remington: *The Science and Practice of Pharmacy, $19^{th}$ Edition*, Gennaro ed., Mack Publishing Co. (1995) pp. 552–554). A fluorophore is optionally included in the mixture to facilitate detection. The sample is spotted on the plate and the sample is run isocratically under capillary flow. In a preferred embodiment, the sample is run under electroosmotic flow in a process called High-Speed TLC (HSTLC). In the case of HSTLC, the plate is first wetted with solvent (e.g., acetonitrile solution in the presence of counterion agent) and an electric field (e.g., 2000 V/cm) is applied. Solvent accumulating at the top of the plate is removed by suction. Applicants have surprisingly discovered that ds DNA of selected ranges of base pair length are separable under isocratic conditions by MIPC using the beads of the present invention as described in Example 6. The isocratic solvent conditions for separating a selected range of DNA base pair length, as determined using MIPC, are used in the TLC and HSTLC methods.

Applicants have determined that the chromatographic separations of double stranded DNA fragments exhibit unique Sorption Enthalpies ($\Delta H_{sorp}$). Two compounds (in this case, DNA fragments of different size) can only be separated if they have different partition coefficients (K). The Nernst partition coefficient is defined as the concentration of an analyte (A) in the stationary phase divided by its concentration in the mobile phase:

$$K = \frac{[A]_s}{[A]_m}$$

The partition coefficient (K) and the retention factor (k) are related through the following equations:

$$K = \frac{n(A)_s V_m}{n(A)_m V_s} \text{ and } k = \frac{n(A)_s}{n(A)_m}$$

the quotient $V_m/V_s$ is also called phase volume ratio ($\Phi$). Therefore:

$k=K\Phi$

To calculate the sorption enthalpies, the following fundamental thermodynamic equations are necessary:

$$\ln K = -\frac{\Delta G_{sorp}}{RT},$$

$$\ln k = -\frac{\Delta G_{sorp}}{RT} + \ln\Phi \text{ and } \Delta G_{sorp} = \Delta H_{sorp} - T\Delta S_{sorp}$$

By transforming the last two equations, one obtains the Van't Hoff equation:

$$\ln k = -\frac{\Delta H_{sorp}}{RT} + \frac{\Delta S_{sorp}}{R} + \ln\Phi$$

From a plot in k versus 1/T, the sorption enthalpy $\Delta H_{sorp}$ can be obtained from the slope of the graph (if a straight line is obtained). $\Delta S_{sorp}$ can be calculated if the phase volume ratio ($\Phi$) is known.

The Sorption Enthalpy $\Delta H_{sorp}$ is positive ($\Delta H_{sorp}>0$) showing the separation is endothermic using acetonitrile as the solvent (FIGS. 3 and 4), and using methanol as the solvent, the Sorption Enthalpy $\Delta H_{sorp}$ is negative ($\Delta H_{sorp}<0$), showing the separation is exothermic (FIG. 5).

The thermodynamic data (as shown in the Examples hereinbelow) reflect the relative affinity of the DNA-counterion agent complex for the beads of the invention and the elution solvent. An endothermic plot indicates a preference of the DNA complex for the bead. An exothermic plot indicates a preference of the DNA complex for the solvent over the bead. The plots shown herein are for alkylated and non-alkylated surfaces as described in the Examples. Most liquid chromatographic separations show exothermic plots.

Other features of the invention will become apparent in the course of the following descriptions of exemplary embodiments which are given for illustration of the invention and are not intended to be limiting thereof.

Procedures described in the past tense in the examples below have been carried out in the laboratory. Procedures described in the present tense have not yet been carried out in the laboratory, and are constructively reduced to practice with the filing of this application.

EXAMPLE 1

Preparation of Nonporous Poly(styrene-divinylbenzene) Particles

Sodium chloride (0.236 g) was added to 354 mL of deionized water in a reactor having a volume of 1.0 liter. The reactor was equipped with a mechanical stirrer, reflux condenser, and a gas introduction tube. The dissolution of the sodium chloride was carried out under inert atmosphere (argon), assisted by stirring (350 rpm), and at an elevated temperature (87° C.). Freshly distilled styrene (33.7 g) and 0.2184 g of potassium peroxodisulfate ($K_2S_2O_8$) dissolved in 50 mL of deionized water were then added. Immediately after these additions, the gas introduction tube was pulled out of the solution and positioned above the liquid surface. The reaction mixture was subsequently stirred for 6.5 hours at 87° C. After this, the contents of the reactor were cooled down to ambient temperature and diluted to a volume yielding a concentration of 54.6 g of polymerized styrene in 1000 mL volume of suspension resulting from the first step. The amount of polymerized styrene in 1000 mL was calculated to include the quantity of the polymer still sticking to the mechanical stirrer (approximately 5–10 g). The diameter of the spherical beads in the suspension was determined by light microscopy to be about 1.0 micron.

Beads resulting from the first step are still generally too small and too soft (low pressure stability) for use as chromatographic packings. The softness of these beads is caused by an insufficient degree of crosslinking. In a second step, the beads are enlarged and the degree of crosslinking is increased.

The protocol for the second step is based on the activated swelling method described by Ugelstad et al. (*Adv. Colloid Interface Sci.,* 13:101–140 (1980)). In order to initiate activated swelling, or the second synthetic step, the aqueous suspension of polystyrene seeds (200 ml) from the first step was mixed first with 60 mL of acetone and then with 60 mL of a 1-chlorododecane emulsion. To prepare the emulsion, 0.206 g of sodium dodecylsulfate, 49.5 mL of deionized water, and 10.5 mL of 1-chlorododecane were brought together and the resulting mixture was kept at 0° C. for 4 hours and mixed by sonication during the entire time period until a fine emulsion of <0.3 microns was obtained. The mixture of polystyrene seeds, acetone, and 1-chlorododecane emulsion was stirred for about 12 hours at room temperature, during which time the swelling of the beads occurred. Subsequently, the acetone was removed by a 30 minute distillation at 80° C.

Following the removal of acetone, the swollen beads were further grown by the addition of 310 g of a ethylvinylbenzene and divinylbenzene (DVB) (1:1.71) mixture also containing 2.5 g of dibenzoylperoxide as an initiator. The growing occurred with stirring and with occasional particle size measurements by means of light microscopy.

After completion of the swelling and growing stages, the reaction mixture was transferred into a separation funnel. In an unstirred solution, the excess amount of the monomer separated from the layer containing the suspension of the polymeric beads and could thus be easily removed. The remaining suspension of beads was returned to the reactor and subjected to a stepwise increase in temperature (63° C. for about 7 hours, 73° C. for about 2 hours, and 83° C. for about 12 hours), leading to further increases in the degree of polymerization (>500). The pore size of beads prepared in this manner was below the detection limit of mercury porosimetry (<30 Å).

After drying, the dried beads (10 g) from step two were washed four times with 100 mL of n-heptane, and then two times with each of the following: 100 mL of diethylether, 100 mL of dioxane, and 100 mL of methanol. Finally, the beads were dried.

EXAMPLE 2

Acid Wash Treatment

The beads prepared in Example 1 were washed three times with tetrahydrofuran and two times with methanol. Finally the beads were stirred in a mixture containing 100 mL tetrahydrofuran and 100 mL concentrated hydrochloric acid for 12 hours. After this acid treatment, the polymer beads were washed with a tetrahydrofuran/water mixture until neutral (pH=7). The beads were then dried at 40° C. for 12 hours.

EXAMPLE 3

Standard Procedure for Testing the Performance of Separation Media

Separation particles are packed in an HPLC column and tested for their ability to separate a standard DNA mixture. The standard mixture is a pUC18 DNA-HaeIII digest (Sigma-Aldrich, D6293) which contains 11 fragments having 11, 18, 80, 102, 174, 257, 267, 298, 434, 458, and 587 base pairs, respectively. The standard is diluted with water and five μL, containing a total mass of DNA of 0.25 μg, is injected.

Depending on the packing volume and packing polarity, the procedure requires selection of the driving solvent concentration, pH, and temperature. The separation conditions are adjusted so that the retention time of the 257, 267 peaks is about 6 to 10 minutes. Any one of the following solvents can be used: methanol, ethanol, 2-propanol, 1-propanol, tetrahydrofuran (THF), or acetonitrile. A counterion agent is selected from trialkylamine acetate, trialkylamine carbonate, trialkylamine phosphate, or any other type of cation that can form a matched ion with the polynucleotide anion.

As an example of this procedure, FIG. 2 shows the high resolution of the standard DNA mixture using octadecyl modified, nonporous poly(ethylvinylbenzene-divinylbenzene) beads. The separation was conducted under the following conditions: Eluent A: 0.1 M TEAA, pH 7.0; Eluent B: 0.1 M TEAA, 25% acetonitrile; Gradient:

| Time (min) | % A | % B |
|---|---|---|
| 0.0 | 65 | 35 |
| 3.0 | 45 | 55 |
| 10.0 | 35 | 65 |
| 13.0 | 35 | 65 |
| 14.0 | 0 | 100 |
| 15.5 | 0 | 100 |
| 16.5 | 65 | 35 |

The flow rate was 0.75 mL/min, detection UV at 260 nm, column temp. 50° C. The pH was 7.0.

As another example of this procedure using the same separation conditions as in FIG. 2, FIG. 3 is a high resolution separation of the standard DNA mixture on a column containing nonporous 2.1 micron beads of underivatized poly(styrene-divinylbenzene).

EXAMPLE 4

Sorption Enthalpy Measurements

Four fragments (174 bp, 257 bp, 267 bp, and 298 bp, found in 5 μL pUC18 DNA-HaeIII digest, 0.04 μg DNA/μL) were separated under isocratic conditions at different temperatures using octadecyl modified, nonporous poly (styrene-divinylbenzene) polymer beads. The separation was carried out using a Transgenomic WAVE™ DNA Fragment Analysis System equipped with a DNASep™ column (Transgenomic, Inc., San Jose, Calif.) under the following conditions: Mobile phase: 0.1 M triethylammonium acetate, 14.25% (v/v) acetonitrile at 0.75 mL/min, detection at 250 nm UV, temperatures at 35, 40, 45, 50, 55, and 60° C., respectively. A plot of ln k versus 1/T shows that the retention factor k is increasing with increasing temperature (FIG. 4). This indicates that the retention mechanism is based on an endothermic process ($\Delta H_{sorp} > 0$).

The same experiments on non-alkylated poly(styrene-divinylbenzene) beads gave a negative slope for a plot of ln k versus 1/T, although the plot is slightly curved (FIG. 5).

Figure 6:
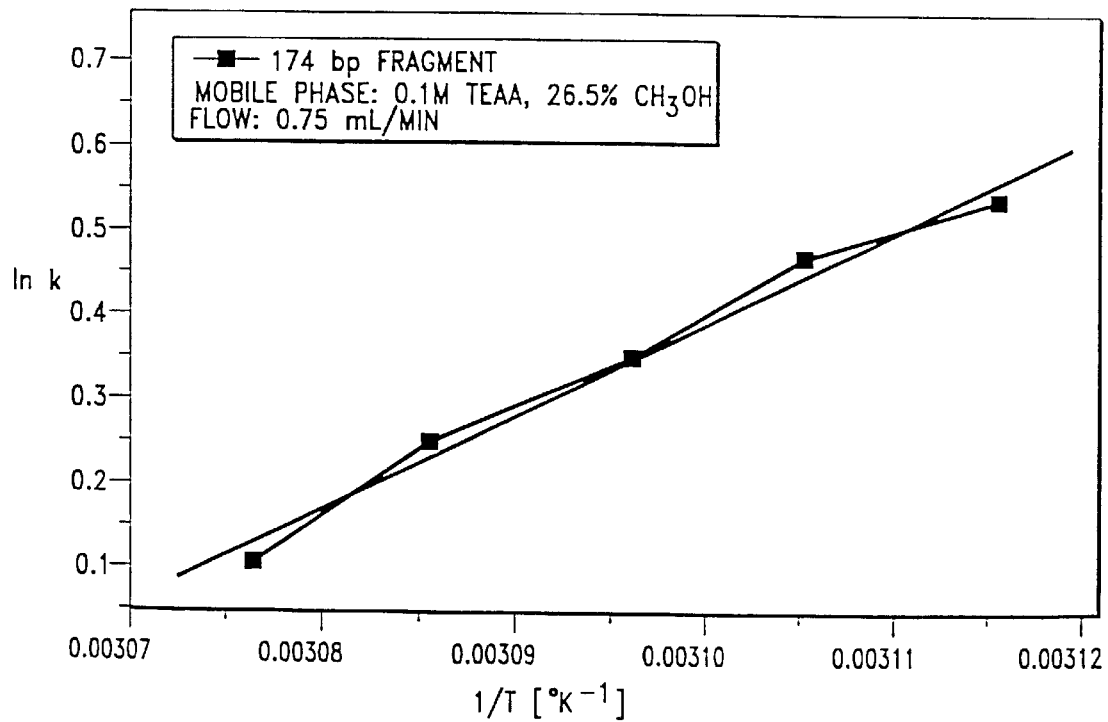
FIG. 6 is a Van't Hoff plot of In k vs. 1/T [°K$^{-1}$] with alkylated poly(styrene-divinylbenzene) beads showing negative enthalpy using methanol as the solvent.

The same experiments performed on octadecyl modified, nonporous poly(styrene-divinylbenzene) beads but with methanol replacing the acetonitrile as solvent gave a plot ln k versus 1/T showing the retention factor k is decreasing with increasing temperature (FIG. 6). This indicates the retention mechanism is based on an exothermic process ($\Delta H_{sorp} < 0$).

EXAMPLE 5

Separations with Alkylated Poly(styrene-divinylbenzene) Beads

Mobile phase components are chosen to match the desorption ability of the elution solvent in the mobile phase to the attraction properties of the bead to the DNA-counterion complex. As the polarity of the bead decreases, a stronger (more organic) or higher concentration of solvent will be required. Weaker organic solvents such as methanol are generally required at higher concentrations than stronger organic solvents such as acetonitrile.

Figure 7:
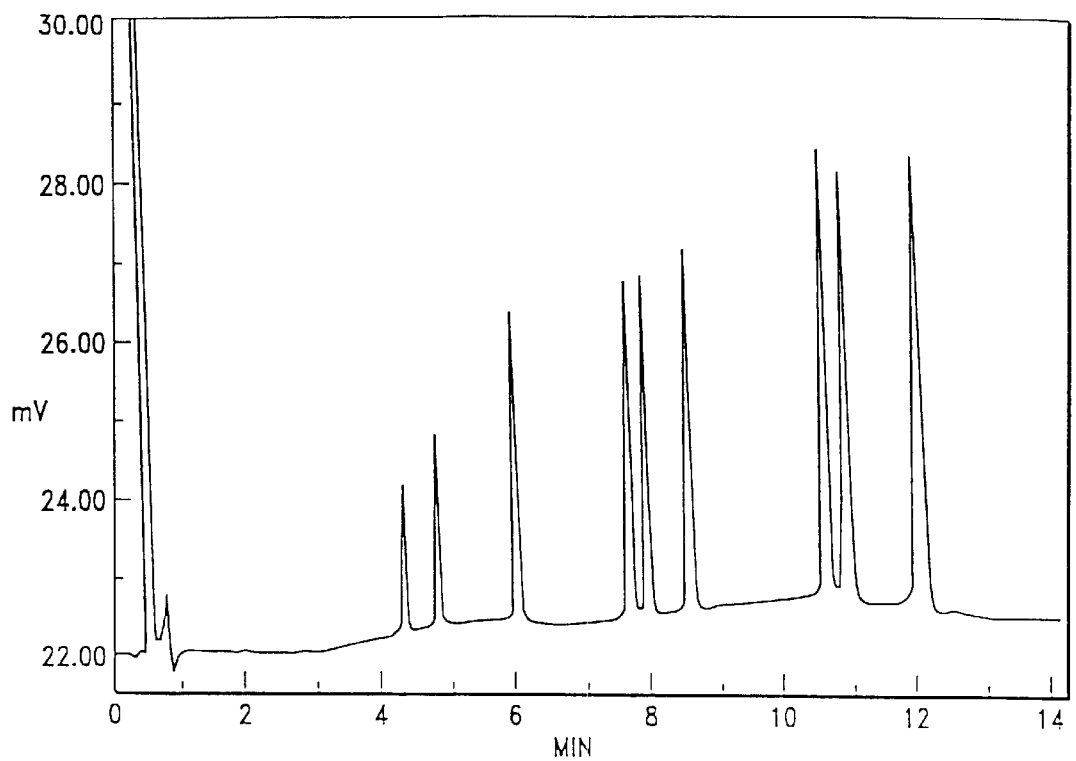
FIG. 7 is a separation using alkylated beads and acetonitrile as solvent.

FIG. 7 shows the high resolution separation of DNA restriction fragments using octadecyl modified, nonporous poly(ethylvinylbenzene-divinylbenzene) beads. The experiment was conducted under the following conditions: Column: 50×4.6 mm I.D.; mobile phase 0.1 M TEAA, pH 7.2; gradient: 33–55% acetonitrile in 3 min, 55–66% acetonitrile in 7 min, 65% acetonitrile for 2.5 min; 65–100% acetonitrile in 1 min; and 100–35% acetonitrile in 1.5 min. The flow rate was 0.75 mL/min, detection UV at 260 nm, column temp. 51° C. The sample was 5 μL (=0.2 μg pUC18 DNA-HaeIII digest).

Figure 8:
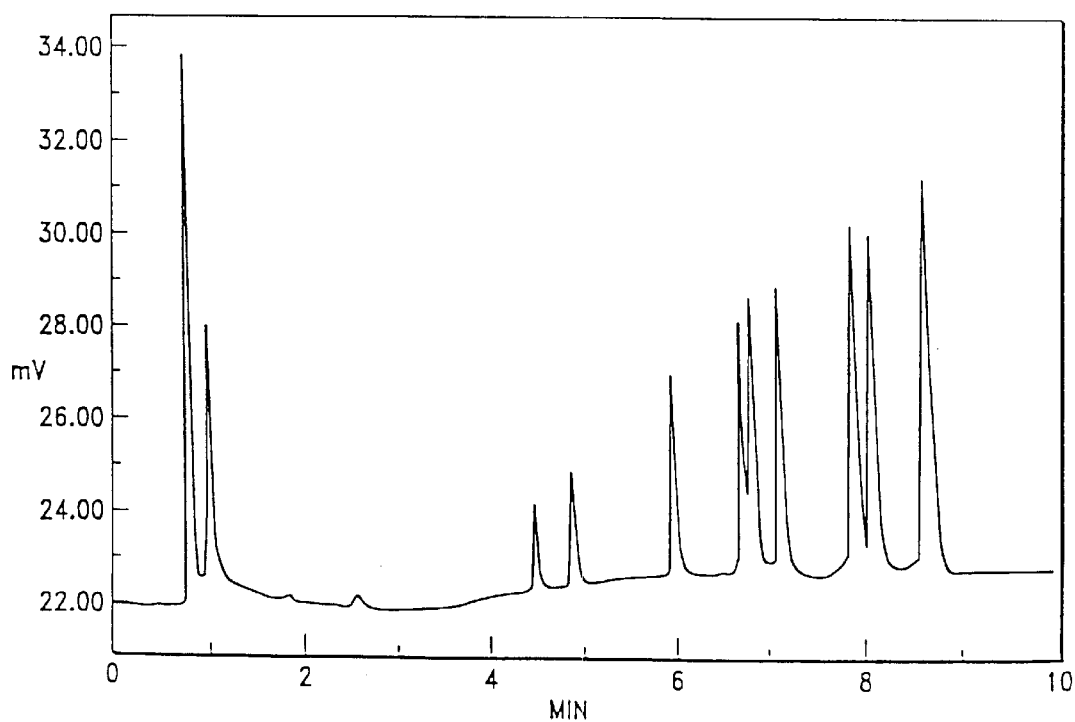
FIG. 8 is a separation using alkylated beads and 50.0% methanol as the solvent.

Repeating the procedure of FIG. 7 replacing the acetonitrile with 50.0% methanol in 0.1 M (TEAA) gave the separation shown in FIG. 8.

Figure 9:
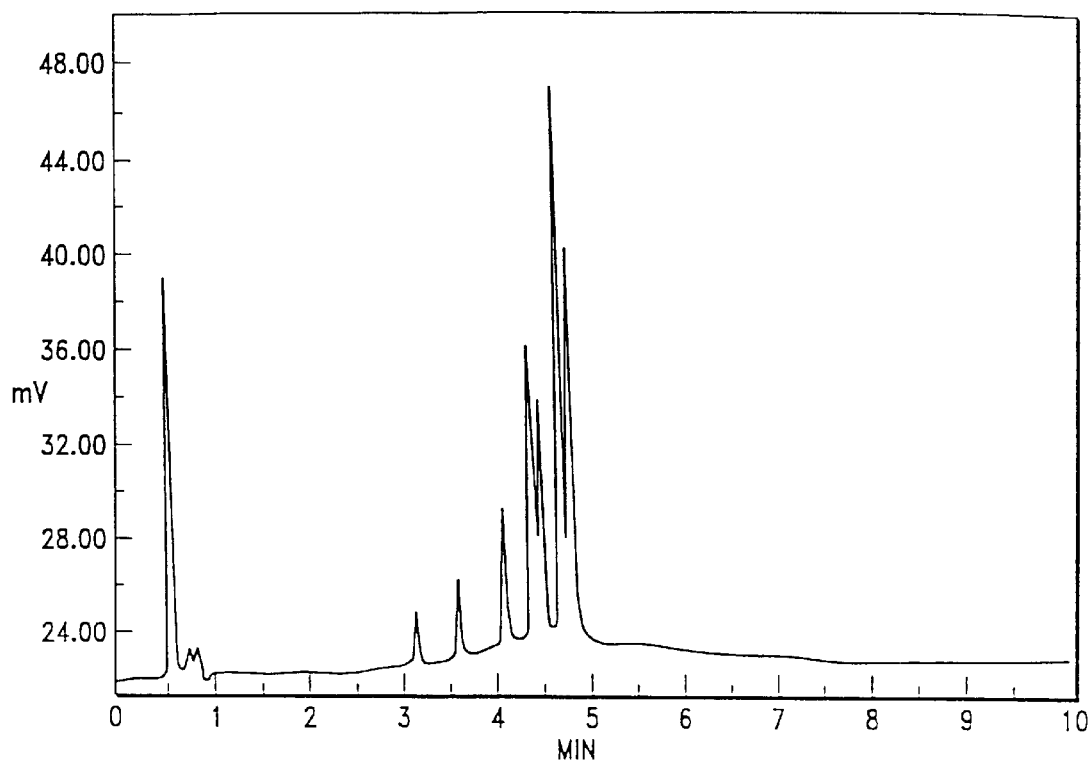
FIG. 9 is a separation using alkylated beads and 25.0% ethanol as the solvent.

Repeating the procedure of FIG. 7 replacing the acetonitrile with 25.0% ethanol in 0.1 M (TEAA) gave the separation shown in FIG. 9.

Figure 10:
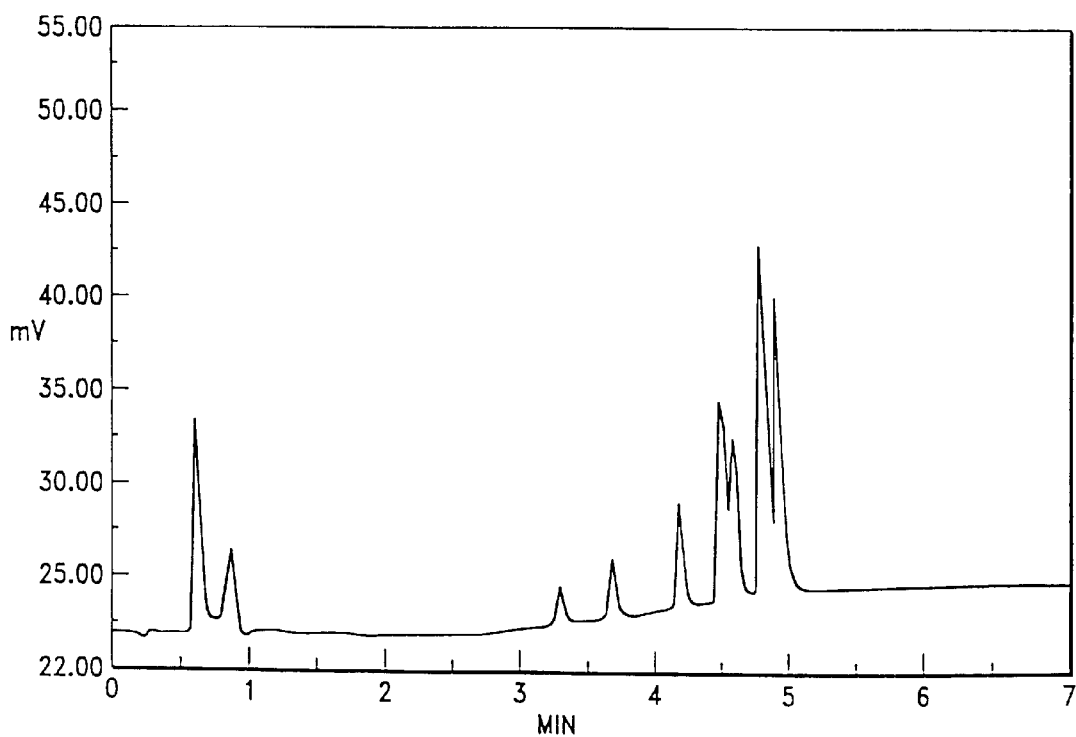
FIG. 10 is a separation using alkylated beads and 25.0% vodka (100 proof) as the solvent.

Repeating the procedure of FIG. 7 replacing the acetonitrile with 25% vodka (Stolichnaya, 100 proof) in 0.1 M (TEAA) gave the separation shown in FIG. 10.

Figure 11:
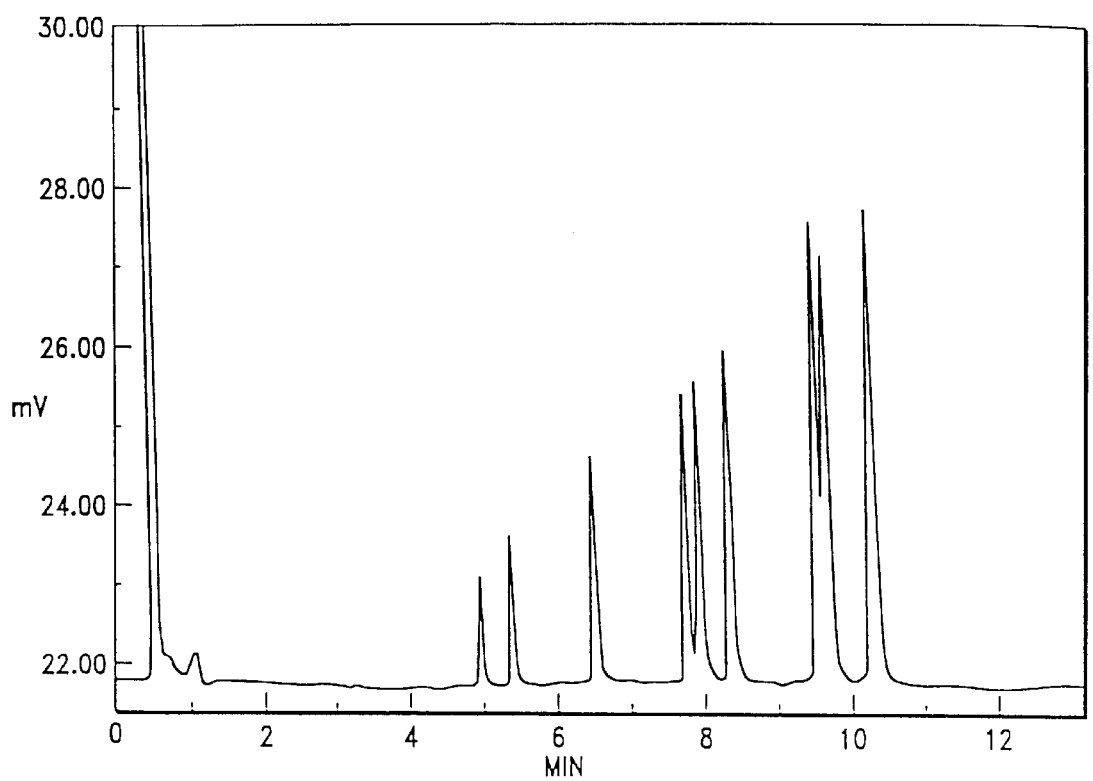
FIG. 11 is a separation using alkylated beads and 25.0% 1-propanol as the solvent.

The separation shown in FIG. 11 was obtained using octadecyl modified, nonporous poly(ethylvinylbenzene-divinylbenzene) beads as follows: Column: 50×4.6 mm I.D.; mobile phase 0.1 M tetraethylacetic acid (TEAA), pH 7.3; gradient: 12–18% 0.1 M TEAA and 25.0% 1-propanol (Eluent B) in 3 min, 18–22% B in 7 min, 22% B for 2.5 min; 22–100% B in 1 min; and 100–12% B in 1.5 min. The flow rate was 0.75 mL/min, detection UV at 260 nm, and column temp. 51° C. The sample was 5 μL (=0.2 μg pUC18 DNA-HaeIII digest).

Figure 12:
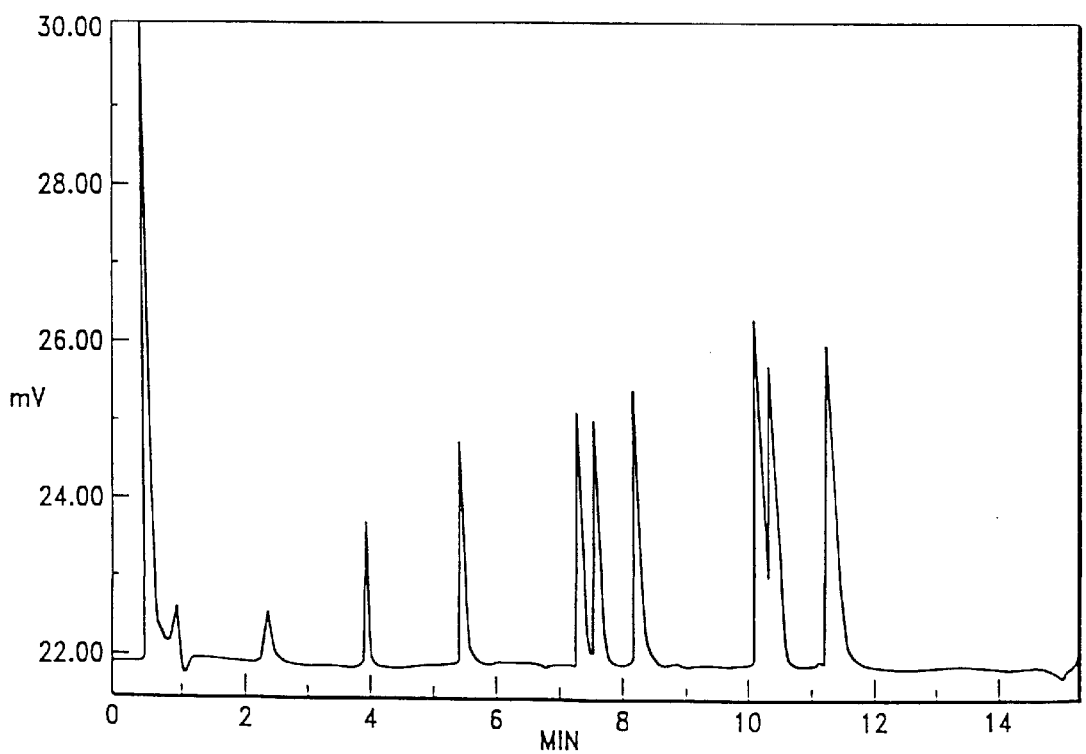
FIG. 12 is a separation using alkylated beads and 25.0% 1-propanol as the solvent.

The separation shown in FIG. 12 was obtained using octadecyl modified, nonporous poly(ethylvinylbenzene-divinylbenzene) beads as follows: Column: 50×4.6 mm I.D.; mobile phase 0.1 M TEAA, pH 7.3; gradient: 15–18% 0.1 M TEAA and 25.0% 1-propanol (Eluent B) in 2 min, 18–21% B in 8 min, 21% B for 2.5 min; 21–100% B in 1 min; and 100–15% B in 1.5 min. The flow rate was 0.75 ml/min, detection UV at 260 nm, and column temp. 51° C. The sample was 5 μL (=0.2 μg pUC18 DNA-HaeIII digest).

Figure 13:
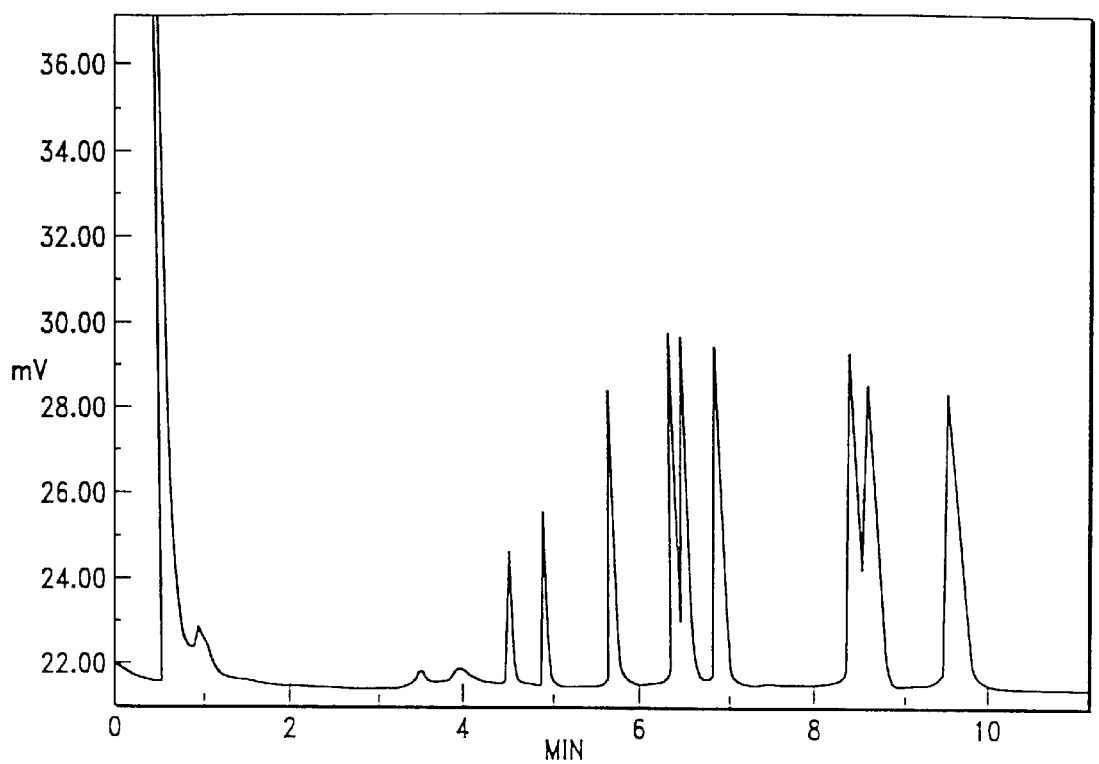
FIG. 13 is a separation using alkylated beads and 10.0% 2-propanol as the solvent.

The separation shown in FIG. 13 was obtained using octadecyl modified, nonporous poly(ethylvinylbenzene-divinylbenzene) beads as follows: Column: 50×4.6 mm I.D.; mobile phase 0.1 M TEAA, pH 7.3; gradient: 35–55% 0.1 M TEAA and 10.0% 2-propanol (Eluent B) in 3 min, 55–65% B in 10 min, 65% B for 2.5 min; 65–100% B in 1 min; and 100–35% B in 1.5 min. The flow rate was 0.75 mL/min, detection UV at 260 nm, and column temp. 51° C. The sample was 5 μL (=0.2 μg pUC18 DNA-HaeIII digest).

Figure 14:
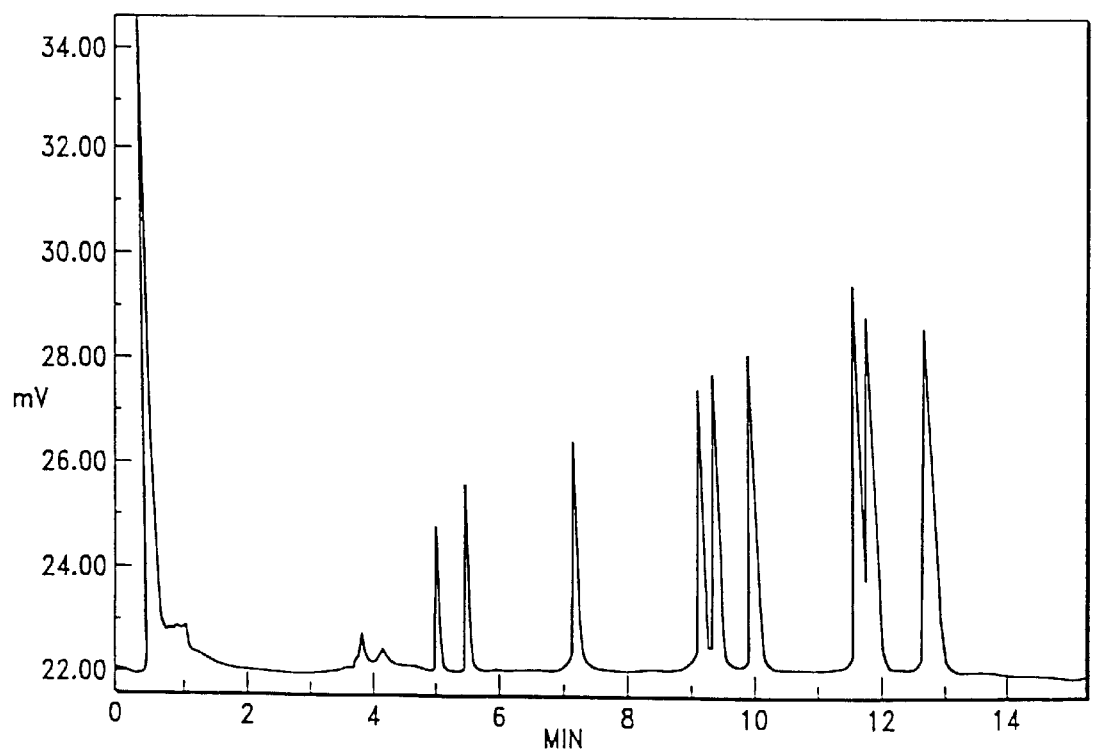
FIG. 14 is a separation using alkylated beads and 10.0% 2-propanol as the solvent.

The separation shown in FIG. 14 was obtained using octadecyl modified, nonporous poly(ethylvinylbenzene-divinylbenzene) beads as follows: Column: 50×4.6 mm I.D.; mobile phase 0.1 M TEA$_2$HPO$_4$, pH 7.3; gradient: 35–55% 0.1 M TEA$_2$HPO$_4$ and 10.0% 2-propanol (Eluent B) in 3 min, 55–65% B in 7 min, 65% B for 2.5 min; 65–100% B in 1 min; and 100–65% B in 1.5 min. The flow rate was 0.75 mL/min, detection UV at 260 nm, and column temp. 51° C. The sample was 5 μL (=0.2 μg pUC18 DNA-HaeIII digest).

The separation shown in FIG. 15 was obtained using octadecyl modified, nonporous poly(ethylvinylbenzene-divinylbenzene) beads as follows: Column: 50×4.6 mm I.D.; mobile phase 0.1 M TEAA, pH 7.3; gradient: 6–9% 0.1 M TEAA and 25.0% THF (Eluent B) in 3 min, 9–11% B in 7 min, 11% B for 2.5 min; 11 –100% B in 1 min; and 100–6% B in 1.5 min. The flow rate was 0.75 mL/min, detection UV at 260 nm, and column temp. 51° C. The sample was 5 μL (=0.2 μg pUC18 DNA-HaeIII digest).

EXAMPLE 6

Isocratic/Gradient Separation of ds DNA

The following is an isocratic/gradient separation of ds DNA using nonporous poly(styrene-divinylbenzene) beads. Isocratic separations have not been performed in DNA separations because of the large differences in the selectivity of DNA/alkylammonium ion pair for beads. However, by using a combination of gradient and isocratic elution conditions, the resolving power of a system can be enhanced for a particular size range of DNA. For example, the range of 250–300 base pairs can be targeted by using a mobile phase of 0.1 M TEAA, and 14.25% acetonitrile at 0.75 mL/min at 40° C. on 50×4.6 mm cross-linked poly(styrene-divinylbenzene) column, 2.1 micron. 5 μL of pUC18 DNA-HaeIII digest (0.2 μg) was injected under isocratic conditions and 257, 267 and 298 base pairs DNA eluted completely resolved as shown in FIG. 16. Then the column was cleaned from larger fragments with 0.1 M TEAA/25% acetonitrile at 9 minutes. In other examples, there might be an initial isocratic step (to condition the column), then a gradient step (to remove or target the first group of DNA at a particular size), then an isocratic step (to separate the target material of a different size range) and finally a gradient step to clean the column.

EXAMPLE 7

Bromination of Remaining Double Bonds on the Surface of Poly(Styrene-Divinylbenzene) Polymer Beads 50.0 g of a poly(styrene-divinylbenzene) polymer beads were suspended in 500 g of tetrachloromethane. The suspension was transferred into a 1000 mL glass reactor (with attached reflux condenser, separation funnel and overhead stirrer). The mixture was kept at 20° C. Bromine (100 mL) was added over a period of 20 minutes. After addition was completed, stirring continued for 60 minutes. The temperature was raised to 50° C. to complete the reaction (2 hours).

The polymer beads were separated from the tetrachloromethane and excess bromine by means of centrifugation and cleaned with tetrahydrofuran (once with 100 mL) and methanol (twice with 100 mL). The polymer beads were dried at 40° C.

The polymer beads are packed into a 50×4.6 mm i.d column and the DNA Separation Factor is greater than 0.05 as tested by the procedure of Example 3.

EXAMPLE 8

Nitration of a Poly(Styrene-Divinylbenzene) Polymer Beads

In a 1000 mL glass reactor 150 mL of concentrated nitric acid (65%) were combined with 100 mL concentrated sulfuric acid. The acid mixture was cooled to 0–4° C. When the temperature had dropped to <4° C., 50 g of poly(styrene-divinylbenzene) polymer beads were added slowly under continuous stirring. After addition was completed, 50 mL of nitric acid (65%) was added. The suspension was stirred for three hours, maintaining a temperature of 5–10° C.

On the next day the reaction was quenched by adding ice to the suspension. The polymer beads were separated from the acid by means of centrifugation. The polymer beads were washed to neutrality with water, followed by washing steps with tetrahydrofurane (four times with 100 mL) and methanol (four times with 100 mL). The polymer beads were dried at 40° C.

The polymer beads are packed into a 50×4.6 mm i.d column and the DNA Separation Factor is greater than 0.05 as tested by the procedure of Example 3.

EXAMPLE 9

Preparation of a Non-Polar Organic Polymer Monolith Chromatography Column

A chromatography tube in which the monolith polymeric separation medium is prepared is made of stainless steel. The monomers, styrene (Sigma - Aldrich Chemical Corp.) and divinylbenzene (Dow Chemical Corp.) are dried over magnesium sulfate and distilled under vacuum.

To a solution of a 1:1 mixture by volume of the distilled styrene and divinylbenzene, containing 1% by weight (with respect to monomers) of azobisisobutyronitrile (AIBN), is added eight volumes of a solution of the porogenic solvent, dodecyl alcohol and toluene (70:30). The solution so prepared is bubbled with nitrogen for 15 minutes and is used to fill a chromatography tube (50×8 mm I.D.) sealed with a rubber nut plug at the bottom end. The tube is then sealed at the top end with a rubber nut plug and the contents are allowed to polymerize at 70° C. for 24 hours.

Following polymerization, the rubber plugs are replaced by column end fittings and the column is connected to an HPLC system. The HPLC instrument has a low-pressure mixing quaternary gradient capability. A cartridge or guard column containing an iminodiacetate multivalent cation capture resin is placed in line between the column and the mobile phase source reservoir. The column is then washed by flowing 100 mL of tetrahydrofuran (THF) at 1 mL/min through the column to remove the dodecyl alcohol and toluene, thereby creating through-pores in the otherwise solid polymer monolith.

In this example, all of the flow paths are either titanium, sapphire, ceramic, or PEEK, except for the tube body, which is 316 stainless steel. The interior of the 316 stainless steel tube is passivated with dilute nitric acid prior to use.

EXAMPLE 10

Acid Wash Treatment To Remove Multivalent Metal Cation Contaminants

The non-polar, organic polymer monolith column is washed by flowing tetrahydrofuran through the column at a flow rate of 2 mL per minute for 10 minutes followed by flowing methanol through the column at 2 mL per minute for 10 minutes. The non-polar, organic polymer monolith column is washed further by flowing a mixture containing 100 mL of tetrahydrofuran and 100 mL of concentrated hydrochloric acid through the column at 10 mL per minute for 20 minutes. Following this acid treatment, the non-polar, organic polymer monolith column is washed by flowing

EXAMPLE 11

Bromination of Remaining Double Bonds on the Surface of Non-Polar Organic Polymer Monolith Column Any double bonds remaining on the surface of the monolith column prepared in Example 9 are reacted with bromine as described in Example 7.

EXAMPLE 12

Nitration of a Non-Polar Organic Polymer Monolith Column

The non-polar organic column prepared in Example 9 is nitrated as described in Example 8.

EXAMPLE 13

Determination of the Mutation Separation Factor

The Mutation Separation Factor (MSF) is determined by the following equation:

MSF=(area peak 2−area peak 1)/area peak 1 where area peak 1 is the area of the peak measured after DMIPC analysis of wild type and area peak 2 is the total area of the peak or peaks measured after DMIPC analysis of a hybridized mixture containing a putative mutation, with the hereinabove correction factors taken into consideration, and where the peak heights have been normalized to the wild type peak height. Separation particles are packed in an HPLC column and tested for their ability to separate a standard hybridized mixture containing a wild type 100 bp Lambda DNA fragment and the corresponding 100 bp fragment containing an A to C mutation at position 51.

Depending on the packing volume and packing polarity, the procedure requires selection of the driving solvent concentration, pH, and temperature. Any one of the following solvents can be used: acetonitrile, tetrahydrofuran, methanol, ethanol, or propanol. Any one of the following counterion agents can be used: trialkylamine acetate, trialkylamine carbonate, and trialkylamine phosphate.

As an example of the determination of the Mutation Separation Factor, FIG. 22 shows the resolution of the separation of the hybridized DNA mixture.

The PCR conditions used with each of the primers are described in the table below. All the components were combined and vortexed to ensure good mixing, and centrifuged. Aliquots were then distributed into PCR tubes as shown in the following table:

| COMPONENT | VOLUME |
|---|---|
| Pfu 10× Buffer (Cat. No. 600153-82, Stratagene, Inc., La Jolla, CA) | 5 μL |
| 100 μM dNTP Mix | 4 μL |
| Primer 1 (forward) | 7.5 μL |
| Primer 2 (reverse) | 8.5 μL |
| H$_2$O | 19.5 μL |
| Lambda DNA Template | 5 μL |
| PFUTurbo ™ (600250, Stratagene) | 0.5 μL |

The PCR tubes were placed into a thermocycler (PTC-100 Programmable Thermal Controller from MJ Research, Inc., Watertown, Mass.) and the temperature cycling program was initiated. The cycling program parameters are shown in the table below:

| STEP | TEMPERATURE | TIME |
|---|---|---|
| 1 | 94° C. | 2 minutes |
| 2 | 94° C. | 1 minute |
| 3 | 58° C. | 1 minute |
| 4 | 72° C. | 1 minute |
| 5 | Go to Step 2, 34× | |
| 6 | 72° C. | 10 minutes |
| 7 | End | |

The DMIPC conditions used for the mutation detection separations are shown below:
Eluent A: 0.1 M TEAA; Eluent B: 0.1 M TEAA, 25% Acetonitrile; Flow rate: 0.90 mL/min; Gradient:

| Time (min) | % A | % B |
|---|---|---|
| 0.0 | 50.0 | 50.0 |
| 0.1 | 45.0 | 55.0 |
| 4.6 | 36.0 | 64.0 |
| 4.7 | 0.0 | 100.0 |
| 5.2 | 0.0 | 100.0 |
| 5.3 | 50.0 | 50.0 |
| 7.8 | 50.0 | 50.0 |

The Lambda sequence has been published by O'Conner et al. in *Biophys. J.* 74:A285 (1998) and by Garner, et al., at the Mutation Detection 97 4th International Workshop, Human Genome Organization, May 29–Jun. 2, 1997, Brno, Czech Republic, Poster no. 29. The 100 bp Lambda fragment sequence (base positions 32011–32110) was used as a standard (available from FMC Corp. available from FMC Corp. BioProducts, Rockland, Me.). The mutation was at position 32061. The chart below lists the primers used:

| Primers |
|---|
| Forward Primer: 5'-GGATAATGTCCGGTGTCATG-3' Reverse Primer: 3'-GGACACAGTCAAGACTGCTA-5' |

FIG. 21 is a chromatogram of the wild type strand analyzed under the above conditions. The peak appearing has a retention time of 4.78 minutes and an area of 98621.

FIG. 22 is the Lambda mutation analyzed in identical conditions as FIG. 21 above. Two peaks are apparent in this chromatogram, with retention times of 4.32 and 4.68 minutes and a total area of 151246.

The Mutation Separation Factor is calculated by applying these various peak areas to the above MSF equation. Thus, using the definition stated hereinabove, MSF=(area peak 2-area peak 1)/area peak 1, the MSF would be (151246-98621)/98621, or 0.533.

EXAMPLE 14

Effect of Multivalent Cation Decontamination Measures on Sample Resolution by DMIPC The separation shown in FIG. 18 was obtained using a WAVE™ DNA Fragment Analysis System (Transgenomic, Inc., San Jose, Calif.) under the following conditions: Column: 50×4.6 mm i.d. containing alkylated poly(styrene-divinylbenzene) beads (DNASep®, Transgenomic, Inc.); mobile phase 0.1 M TEAA (1 M concentrate available from Transgenomic, Inc.) (Eluent A), pH 7.3; gradient: 50–53% 0.1 M TEAA and 25.0% acetonitrile (Eluent B) in 0.5 min; 53–60% B in 7 min; 60–100% B in 1.5 min; 100–50% B in 1 min; 50% B for 2 min. The flow rate was 0.9 mL/min, UV detection was at 254 nm, and the column temperature was 56° C. The sample was 2 μL (=0.2 μg DNA, DYS271 209 bp mutation standard with an A to G mutation at position 168).

FIG. 19 is the same separation as performed in FIG. 18, but after changing the guard cartridge (20×4.0 mm, chelating cartridge, part no. 530012 from Transgenomic, Inc.) and replacing the pump-valve filter (Part no. 638–1423, Transgenomic, Inc.). The guard cartridge had dimensions of 10×3.2 mm, containing iminodiacetate chelating resin of 2.5 mequiv/g capacity and 10 μm particle size, and was positioned directly in front of the injection valve.

FIG. 20 is the same separation as performed in FIG. 19, but after flushing the column for 45 minutes with 0.1 M TEAA, 25% acetonitrile, and 32 mM EDTA, at 75° C.

EXAMPLE 15

Hybridization of Mutant and Wild Type DNA Fragments

Figure 17:
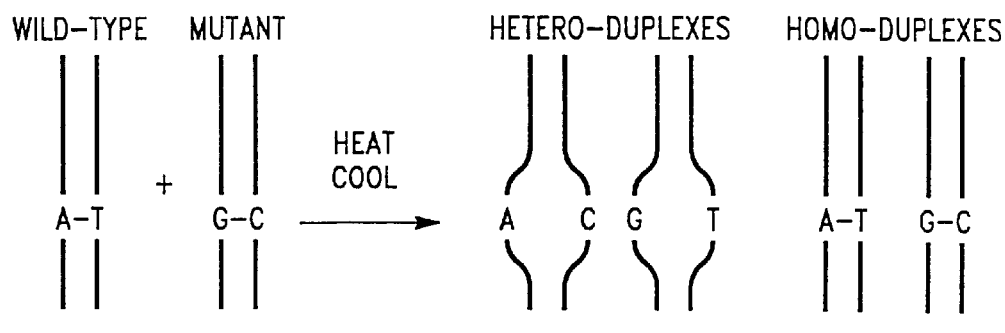
FIG. 17 shows a schematic representation of a hybridization to form homoduplex and heteroduplex.

A mixture of two homoduplexes and two heteroduplexes was produced by a hybridization process. In this process, a DYS271 209 bp mutation standard containing a mixture of the homozygous mutant DNA fragment (with an A to G mutation at position 168) combined with the corresponding wild type fragment in an approximately 1:1 ratio (the mixture is available as a Mutation Standard from Transgenomic, Inc., San Jose, Calif.; the mutation is described by Seielstad et al., Human Mol. Genet. 3:2159 (1994)) was heated at 95° C. for 3–5 minutes then cooled to 25° C. over 45 minutes. The hybridization process is shown schematically in FIG. 17.

EXAMPLE 16

Alkylation of Poly(Styrene-Divinylbenzene) Polymer Beads

The following procedures were carried out under nitrogen (Air Products, Ultra Pure grade, Allentown, Pa.) at a flow rate of 250–300 mL/min. 25 g of the beads prepared in Example 1 were suspended in 150–160 g of 1-chlorooctadecane (product no. 0235, TCI America, Portland, Oreg.) using a bow shaped mixer (use a 250 mL wide neck Erlenmeyer flask). The temperature was set to 50–60° C. to prevent the 1-chlorooctadecane from solidifying. Larger pieces of polymer were broken up to facilitate suspending. The solution was mixed using a stirrer (Model RZRI, Caframo, ONT NOH2T0, Canada) with the speed set at 2. The polymer suspension was transferred into a three neck bottle (with reflux condenser, overhead stirrer and gas inlet). 52–62 g of 1-chlorooctadecane were used to rinse the Erlenmeyer flask and were added to the three neck bottle. The bottle was heated in an ethylene glycol bath set at 80° C. The solution was mixed using a stirrer (Caframo) with the speed set at 0. After 20 minutes, the reaction was started by addition of 1.1 g $AlCl_3$ powder (product no. 06218, Fluka, Milwaukee, Wis.) and continued for 16–18 h.

After the reaction, the polymer was separated from excess 1-chlorooctadecane by centrifugation followed by consecutive washing steps:

| Addition | Comment |
| --- | --- |
| 50 mL conc. HCl, 50–60 mL n-heptane | 4 repetitions, with recycled heptane |
| 100 mL $H_2O$, 50–60 mL n-heptane | 1 repetition, with fresh heptane |
| 50 mL conc. HCl, 50–60 mL n-heptane | 1 repetition, with fresh heptane |
| 100 mL $H_2O$, 50–60 mL n-heptane | 1 repetition, fresh heptane |
| 150 mL $H_2O$, no n-heptane | 3 repetitions, use plastic stirrer to break up chuncks of polymer beads. Repeat steps 4 and 5 three times. Shake for two minutes with no centrifugation. |
| 100 mL THF | 3 repetitions |
| 100 mL THF/n-heptane | 1 repetition |
| 100 mL n-heptane | 1 repetition |
| 100 mL THF | 1 repetition |
| 100 mL $CH_3OH$ | 4 repetitions |

In the steps where aqueous solvents (HCl or $H_2O$) were used, the polymer was shaken for 30 seconds with the aqueous phase before adding n-heptane. n-Heptane was then added and the mixture was shaken vigorously for 2 min.

After the final polymeric beads were dried at 40–50° C. for 2–3 hr it was ready for packing.

EXAMPLE 17

Column Packing Procedure

After weighing out 1.2 grams of oven dried polymeric beads, form a slurry with 10 mL tetrahydrofuran (THF) and place in a sonicator under a fume hood for 15 min. The add 5 mL of THF and 5 mL of methanol (MeOH) and sonicate an additional 10 min. Pre-fill a packing assembly with 20 mL MeOH. Pour the slurry slowly into the packing assembly. Turn on a Haskel pump (Haskel International, Inc., Burbank, Calif.) and slowly increase packing pressure to 5000 psi for the initial packing phase. After 10 min, slowly increase packing pressure to 9000 psi and set the secondary packing phase for 20 min. After 20 min, change the packing eluent from MeOH to 0.05 M $Na_4EDTA$. The set the final packing phase for 40 min.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

The invention claimed is:

1. A polymeric monolith having nonpolar separation surfaces which has been subjected to an acid wash treatment in order to substantially remove multivalent cation contaminants from the interstitial non-polar separation surfaces that can interfere with the separation of polynucleotides when said monolith is used in separating polynucleotides by reverse phase ion pairing chromatography.

2. A monolith of claim 1 characterized by having a DNA Separation Factor of at least 0.05.

3. A monolith of claim 1 characterized by having a Mutation Separation Factor of at least 0.1.

4. The monolith of claim 1 wherein said multivalent ions comprise multivalent cations that can interfere with the separation of polynucleotides when said monolith is used in separating polynucleotides by reverse phase ion pairing chromatography.

5. The monolith of claim 1 wherein said multivalent cations comprise a member selected from the group consisting of Fe(III), Cr(III), colloidal metal contaminants and mixture of one or more thereof.

6. The monolith of claim 1 wherein said monolith is characterized by having surface pores of a size which essentially exclude polynucleotides being separated from entering said surface pores when said monolith is used in separating polynucleotides by reverse phase ion pairing chromatography.

7. The monolith of claim 1 wherein said monolith comprises a member selected from the group consisting of monovinyl substituted aromatic compound, divinyl substituted aromatic compound, acrylate, methacrylate, polyolefin, polyester, polyurethane, polyamide, polycarbonate, fluoro-substituted ethylene, and combinations of one or more thereof.

8. The monolith of claim 1 wherein said monolith is composed of a polymer selected from the group consisting of styrene, substituted sytrenes, alpha-substituted sytrenes, divinylbenzene, acrylates methacrylates, polypropylene, polyolefins, polyesters, polyurethanes, polyamides, polycarbonates, and fluorosubstituted ethylenes, and combinations of one or more thereof.

9. The monolith of claim 8 wherein said polyolefins are selected from the group consisting of polypropylene and polyethylene.

10. The monolith of claim 1 wherein said monolith is composed of a polymer selected from the group consisting of poly(glycidyl methacrylate-co-ethylene dimethacrylate), poly(styrene-divinylbenzene), and poly(ethylvinylbenzene-divinylbenzene).

11. The monolith of claim 1 wherein said monolith comprises poly(glycidyl methacrylatecoethylene dimethacrylate).

12. A polymeric monolith having non-polar separation surfaces wherein said surfaces are characterized by being substantially free from multivalent cations that can interfere with the separation of polynucleotides when said monolith is used in separating polynucleotides by reverse phase ion pairing chromatography.

13. The monolith of claim 12 wherein said multivalent cations comprise a member selected from the group consisting of Fe(III), Cr(III), colloidal metal contaminants and mixture of one or more thereof.

14. The monolith of claim 12 wherein said monolith has been subjected to acid wash treatment to remove any residual surface metal contaminants.

15. The monolith of claim 12 wherein said monolith has been subjected to treatment with multivalent cation binding agent.

16. The monolith of claim 12 wherein said monolith is characterized by having surface pores of a size which essentially exclude polynucleotides being separated from entering said surface pores when said monolith is used in separating polynucleotides by reverse phase ion pairing chromatography.

17. The monolith of claim 12 wherein said monolith comprises a member selected from the group consisting of monovinyl substituted aromatic compound, divinyl substituted aromatic compound, acrylate, methacrylate, polyolefin, polyester, polyurethane, polyamide, polycarbonate, fluoro-substituted ethylene, and combinations of one or more thereof.

18. The monolith of claim 12 wherein said monolith is composed of a polymer selected from the group consisting of styrene, substituted sytrenes, alpha-substituted sytrenes, divinylbenzene, acrylates methacrylates, polypropylene, polyolefins, polyesters, polyurethanes, polyamides, polycarbonates, and fluorosubstituted ethylenes, and combinations of one or more thereof.

19. The monolith of claim 18 wherein said polyolefins are selected from the group consisting of polypropylene and polyethylene.

20. The monolith of claim 12 wherein said monolith is composed of a base polymer selected from the group consisting of poly(glycidyl methacrylate-co-ethylene dimethacrylate), poly(styrene-divinylbenzene), and poly(ethylvinylbenzene-divinylbenzene).

21. The monolith of claim 12 wherein said monolith comprises poly(glycidyl methacrylatecoethylene dimethacrylate).

22. The monolith of claim 12 characterized by having a DNA Separation Factor of at least 0.05.

23. The monolith of claim 12 characterized by having a DNA Separation Factor of at least 0.1.

24. The monolith of claim 15 wherein said multivalent cation binding agent comprises EDTA.

* * * * *